United States Patent
Kawashima et al.

(10) Patent No.: US 11,040,349 B2
(45) Date of Patent: Jun. 22, 2021

(54) TESTING DEVICE FOR QUANTITATIVE PCR

(71) Applicants: Yudai Kawashima, Kanagawa (JP); Satoshi Izumi, Tokyo (JP); Manabu Seo, Kanagawa (JP)

(72) Inventors: Yudai Kawashima, Kanagawa (JP); Satoshi Izumi, Tokyo (JP); Manabu Seo, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 280 days.

(21) Appl. No.: 16/196,790

(22) Filed: Nov. 20, 2018

(65) Prior Publication Data
US 2019/0151843 A1   May 23, 2019

(30) Foreign Application Priority Data

Nov. 21, 2017 (JP) .............................. JP2017-224014
Mar. 30, 2018 (JP) .............................. JP2018-069068
(Continued)

(51) Int. Cl.
*B01L 3/00* (2006.01)
*B01L 3/02* (2006.01)
(Continued)

(52) U.S. Cl.
CPC .......... *B01L 3/5085* (2013.01); *B01L 3/0268* (2013.01); *C12Q 1/686* (2013.01); *C12Q 1/6844* (2013.01);
(Continued)

(58) Field of Classification Search
CPC ................. B01L 3/5085; B01L 3/0268; B01L 2200/0647; B01L 2200/148;
(Continued)

(56) References Cited

U.S. PATENT DOCUMENTS

| 2003/0165832 A1 | 9/2003 | Sagner et al. |
| 2004/0153254 A1 | 8/2004 | Sagner et al. |

(Continued)

FOREIGN PATENT DOCUMENTS

| AU | 20172120167 A1 | 8/2018 |
| JP | 2002-082120 A | 3/2002 |

(Continued)

OTHER PUBLICATIONS

Espacenet Machine English Translation (Year: 2008).*
(Continued)

*Primary Examiner* — Michael L Hobbs
*Assistant Examiner* — Lenora A Abel
(74) *Attorney, Agent, or Firm* — Oblon, McClelland, Maier & Neustadt, L.L.P.

(57) ABSTRACT

Provided is a device including: at least one well in which an amplifiable reagent is contained in a specific copy number of less than 100; and at least one well in which the amplifiable reagent is contained in a specific copy number of 100 or greater, wherein for the at least one well in which the specific copy number of the amplifiable reagent is less than 100, a formula: $CV < 1/\sqrt{x}$ is established, where CV represents a coefficient of variation for the specific copy number and x represents average specific copy number of the amplifiable reagent.

16 Claims, 17 Drawing Sheets

Specification includes a Sequence Listing.

US 11,040,349 B2
Page 2

(30) Foreign Application Priority Data

Jun. 14, 2018 (JP) .............................. JP2018-114004
Nov. 14, 2018 (JP) .............................. JP2018-213535

(51) Int. Cl.
| | |
|---|---|
| G01N 15/14 | (2006.01) |
| C12Q 1/686 | (2018.01) |
| C12Q 1/6844 | (2018.01) |
| G01N 15/10 | (2006.01) |

(52) U.S. Cl.
CPC ..... *G01N 15/1459* (2013.01); *G01N 15/1463* (2013.01); *B01L 2200/0647* (2013.01); *B01L 2200/148* (2013.01); *B01L 2200/16* (2013.01); *B01L 2300/024* (2013.01); *B01L 2300/0829* (2013.01); *B01L 2400/0415* (2013.01); *B01L 2400/0439* (2013.01); *B01L 2400/0481* (2013.01); *G01N 2015/1006* (2013.01); *G01N 2015/1486* (2013.01)

(58) Field of Classification Search
CPC ........... B01L 2200/16; B01L 2300/024; B01L 2300/0829; B01L 2400/0415; B01L 2400/0439; B01L 2400/0481; C12Q 1/6844; C12Q 1/686; G01N 15/1459; G01N 15/1463; G01N 2015/1006; G01N 2015/1486
USPC ...................................................... 435/305.2
See application file for complete search history.

(56) References Cited

U.S. PATENT DOCUMENTS

| | | | |
|---|---|---|---|
| 2005/0032192 | A1 | 2/2005 | Vesey et al. |
| 2007/0299254 | A1 | 12/2007 | Becker et al. |
| 2008/0182301 | A1 | 7/2008 | Handique et al. |
| 2009/0226958 | A1 | 9/2009 | Vesey et al. |
| 2010/0021923 | A1 | 1/2010 | Sagner et al. |
| 2010/0105049 | A1 | 4/2010 | Ehrich et al. |
| 2011/0118145 | A1 | 5/2011 | Akmaev et al. |
| 2012/0270222 | A1 | 10/2012 | Sagner et al. |
| 2016/0319339 | A1 | 11/2016 | Akmaev et al. |

FOREIGN PATENT DOCUMENTS

| | | | |
|---|---|---|---|
| JP | 2003-265190 A | | 9/2003 |
| JP | 2008-511327 A | | 4/2008 |
| JP | 2008-141965 A | | 6/2008 |
| JP | 2008141965 A | * | 6/2008 |
| JP | 4414220 B2 | | 11/2009 |
| JP | 2010-533490 A | | 10/2010 |
| JP | 5123213 B2 | | 11/2012 |
| JP | 2013-510580 A | | 3/2013 |
| JP | 2015-195735 A | | 11/2015 |
| JP | 2016-000057 A | | 1/2016 |
| JP | 6093934 B2 | | 2/2017 |
| JP | 2018-000112 A | | 1/2018 |
| JP | 2018-093863 A | | 6/2018 |
| JP | 2018-096789 A | | 6/2018 |
| WO | WO 2011/060240 A1 | | 5/2011 |
| WO | WO2017/056251 A1 | | 4/2017 |
| WO | WO 2017/130707 A1 | | 8/2017 |
| WO | WO 2018/110438 A1 | | 6/2018 |

OTHER PUBLICATIONS

Extended European Search Report dated Feb. 1, 2019 in Patent Application No. 18207120.9, citing documents AA-AE, AO-AP, and AX therein, 8 pages.

Deprez, L. et al. "Validation of a digital PCR method for quantification of DNA copy number concentrations by using a certified reference material" Biomolecular Detection and Quantification, vol. 9, XP55458498, 2016, pp. 29-39.

U.S. Food and Drug Administration. "Guidance for Industry: Bioanalytical Method Validation.":<http://www.fda.gov/downloads/Drugs/GuidanceComplianceRegulatoryInformation/Guidances/UCM070107.pdf>, 2001.

European Medicines Agency. "Guideline on Bioanalytical Method Validation.": <http://www.ema.europa.eu/docs/en_GB/document_library/Scientific_guideline/2011/08/WC500109686.pdf>, Jul. 21, 2011).

Dong et al,—"Comparison of four digital PCR platforms for accurate quantification of DNA copy number of a certified plasmid DNA reference material". Scientific reports, (Aug. 25, 2015) 5:13174, DOI:10.1038/srep13174.

Pinheiro et al.—"Evaluation of a Droplet Digital Polymerase Chain Reaction Format for DNA Copy Number Quantification", Anal Chem., vol. 84 No. 2 p. 1003-1011 (2012), DOI:10.1021/ac202578x.

Ihira et al.—"Development of real-time RT-PCR assays for detection of three classes of HHV-6A gene transcripts". J Med Virol., vol. 89, p. 1830-1836(Jun. 2017), DOI:10.1002/jmv.24862.

Japanese First Office Action dated May 1, 2018 for the corresponding Japanese Application No. 2018-069068.

Japanese Second Office Action dated Jul. 31, 2018 for the corresponding Japanese Application No. 2018-069068.

U.S. Appl. No. 16/007,274, filed Jun. 13, 2018.
U.S. Appl. No. 16/041,603, filed Jul. 20, 2018.

* cited by examiner

Levels of copy numbers of amplifiable reagent

FIG. 7

Wells filled with amplifiable reagent ← → ← Wells filled with sample →

| | | | | | | | |
|---|---|---|---|---|---|---|---|
| 1 | $10^2$ | | | | | | |
| 2 | $10^3$ | | | | | | |
| 3 | $10^4$ | | | | | | |
| 10 | $10^5$ | | | | | | |
| 50 | $10^6$ | | | | | | |

FIG. 8

Wells filled with amplifiable reagent ← → ← Wells filled with sample →

| | | | | | | | |
|---|---|---|---|---|---|---|---|
| 1 | $10^2$ | | | | | | |
| 3 | $10^3$ | | | | | | |
| 5 | $10^4$ | | | | | | |
| 10 | $10^5$ | | | | | | |
| 50 | $10^6$ | | | | | | |

350₁  350₂

350₁  350₂

SEQUENCE LISTING

```
<160> NUMBER OF SEQ ID NOS: 3

<210> SEQ ID NO 1
<211> LENGTH: 600
<212> TYPE: DNA
<213> ORGANISM: Artificial Sequence
<220> FEATURE:
<223> OTHER INFORMATION: Synthetic nucleotide

<400> SEQUENCE: 1
attcgaaggg tgattggatc ggagatagga tgggtcaatc gtagggacaa tcgaagccag      60
aatgcaaggg tcaatggtac gcagaatgga tggcacttag ctagccagtt aggatccgac     120
tatccaagcg tgtatcgtac ggtgtatgct tcggagtaac gatcgcacta agcatggctc     180
aatcctaggc tgataggttc gcacatagca tgccacatac gatccgtgat tgctagcgtg     240
attcgtaccg agaactcacg ccttatgact gcccttatgt caccgcttat gtctcccgag     300
atcacacccg ttatctcagc cctaatctct gcggtttagt ctggccttaa tccatgcctc     360
atagctaccc tcataccatc gctcatacct tccgacattg catccgtcat tccaaccctg     420
attcctacgg tctaacctag cctctatcct acccagttag gttgcctctt agcatccctg     480
ttacgtacgc tcttaccatg cgtcttacct tggcactatc gatgggagta tggtagcgag     540
tatggaacgg actaacgtag gcagtaagct agggtgtaag gttgggacta aggatgccag     600

<210> SEQ ID NO 2
<211> LENGTH: 85
<212> TYPE: DNA
<213> ORGANISM: Norwalk virus (GI)

<400> SEQUENCE: 2
cgctggatgc gcttccatga cctcggattg tggacaggag atcgcgatct tctgcccgaa      60
ttcgtaaatg atgatggcgt ctaag                                            85

<210> SEQ ID NO 3
<211> LENGTH: 98
<212> TYPE: DNA
<213> ORGANISM: Norwalk virus (GII)

<400> SEQUENCE: 3
caagagccaa tgttcagatg gatgagattc tcagatctga gcacgtggga gggcgatcgc      60
aatctggctc ccagctttgt gaatgaagat ggcgtcga                              98
```

US 11,040,349 B2

TESTING DEVICE FOR QUANTITATIVE PCR

CROSS-REFERENCE TO RELATED APPLICATIONS

The present application claims priority under 35 U.S.C. § 119 to Japanese Patent Application No. 2017-224014 filed Nov. 21, 2017, Japanese Patent Application No. 2018-069068 filed Mar. 30, 2018, Japanese Patent Application No. 2018-114004 filed Jun. 14, 2018, and Japanese Patent Application No. 2018-213535 filed Nov. 14, 2018. The contents of which are incorporated herein by reference in their entirety.

BACKGROUND OF THE INVENTION

Field of the Invention

The present disclosure relates to a device.

Description of the Related Art

Quantitative PCR methods are techniques for timely detecting the amount of fluorescence corresponding to DNA amplification in the process of a polymerase chain reaction (PCR), and are methods for indirectly quantifying the initial amounts of DNA, cDNA, and RNA. Quantification needs a calibration curve expressing the relationship between a series of nucleic acid samples and corresponding measured values.

In order to obtain a correct quantitative value, what are reported to be needed are that variation of individual measured values, expressed by the coefficient of variation CV, be 20% or lower, that a series of nucleic acid samples include three or more levels, and that five or more measurements be obtained per level (for example, see U.S. Food and Drug Administration. "Guidance for Industry: Bioanalytical Method Validation.": www.fda.gov/downloads/Drugs/Guidance Compliance_Regulatory_Information/Guidances/UCM070107.pdf. 2001, and European Medicines Agency. "Guideline on Bioanalytical Method Validation": wWW.ema.europa.eu/docs/en_GB/document_library/Scientific_guideline/2011/08/WC500109686.pdf. 2011). Such a series of nucleic acid samples are produced by serial dilution of a nucleic acid sample having a known concentration.

For example, there has been proposed a PCR reaction plate container obtained by producing a series of nucleic acid samples by the serial dilution method and sealing a plurality of different filling copy number levels of nucleic acid samples in a plurality of sample filling portions of a container provided with the sample filling portions (for example, see Japanese Unexamined Patent Application Publication No. 2008-141965).

Recently, there has also been proposed a technique of fractionating cells into which a target nucleic acid sequence is introduced, one cell by one cell with a manipulator, to enable measurement and filling of very trace nucleic acid molecules (for example, see Japanese Unexamined Patent Application Publication No. 2015-195735).

SUMMARY OF THE INVENTION

A device of the present disclosure includes at least one well in which an amplifiable reagent is contained in a specific copy number of less than 100, and at least one well in which the amplifiable reagent is contained in a specific copy number of 100 or greater. For the at least one well in which the specific copy number of the amplifiable reagent is less than 100, a formula: $CV < 1/\sqrt{x}$ is established, where CV represents a coefficient of variation for the specific copy number and x represents average specific copy number of the amplifiable reagent.

BRIEF DESCRIPTION OF THE DRAWINGS

FIG. 7 is a diagram illustrating an example of positions of wells filled with an amplifiable reagent in a device of the present disclosure;

FIG. 8 is a diagram illustrating another example of positions of wells filled with an amplifiable reagent in a device of the present disclosure;

DESCRIPTION OF THE EMBODIMENTS

Figure 1:
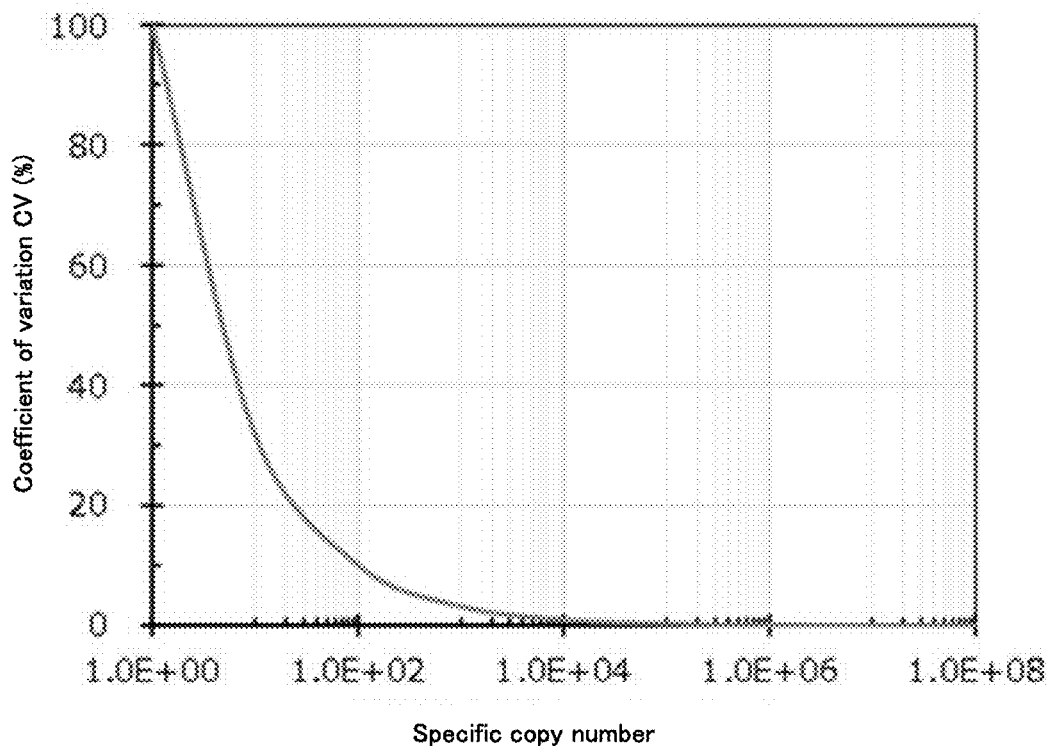
FIG. 1 is a graph plotting a relationship between a copy number having variation according to a Poisson distribution and a coefficient of variation CV.

The present disclosure has an object to provide a device that enables a highly accurate measurement in a wide range varying from a low copy number to a high copy number.

The present disclosure can provide a device that enables a highly accurate measurement in a wide range varying from a low copy number to a high copy number.

(Device)

A device of the present disclosure includes at least one well in which an amplifiable reagent is contained in a specific copy number of less than 100, and at least one well in which the amplifiable reagent is contained in a specific copy number of 100 or greater. For the at least one well in which the specific copy number of the amplifiable reagent is less than 100, a formula: $CV < 1/\sqrt{x}$ is established, where CV represents a coefficient of variation for the specific copy number and x represents average specific copy number of the amplifiable reagent. The device further includes other members as needed.

The device of the present disclosure is based on a finding that existing quantification of samples having unknown concentrations using a calibration curve that is based on serial dilution of a nucleic acid sample results in a significantly poor accuracy in the case of quantification of very trace nucleic acids.

This is considered due to variation (coefficient of variation) in filling a series of nucleic acid samples produced by the serial dilution method. That is, solute molecules of, for example, a nucleic acid sample, while being dissolved in solvent molecules, migrate through the solvent molecules due to thermal fluctuation. In this case, the distribution state of the molecules is generally said to conform to a Poisson distribution. This indicates that a specific copy number of the nucleic acid sample in the solution filled in a container has a distribution, i.e., a variation (coefficient of variation), regardless of with what level of accuracy the solution having a prescribed concentration is weighed out and filled in the container. When the same base sequence is not to be introduced in a plural number into one molecule, "a number of molecules" may be used in the same meaning as "a specific copy number".

Here, the coefficient of variation means a relative value of the variation in the number of cells (or the number of amplifiable reagents) filled in each concave, where the variation occurs when cells are filled in the concave. That is, the coefficient of variation means the filling accuracy in terms of the number of cells (or amplifiable reagents) filled in the concave. The coefficient of variation is a value obtained by dividing standard deviation σ by an average value x. Here, the coefficient of variation CV is assumed to be a value obtained by dividing standard deviation σ by an average copy number (average number of copies filled) x. In this case, a relational expression represented by Formula 1 below is established.

$$CV = \frac{\sigma}{x} \qquad \text{Formula 1}$$

Generally, cells (or amplifiable reagents) have a random distribution state of a Poisson distribution in a dispersion liquid. Therefore, in a random distribution state by a serial dilution method, i.e., of a Poisson distribution, standard deviation σ can be regarded as satisfying a relational expression represented by Formula 2 below with an average copy number x. Hence, in the case where a dispersion liquid of cells (or amplifiable reagents) is diluted by a serial dilution method, when coefficients of variation CV (CV values) for average copy numbers x are calculated according to Formula 3 below derived from Formula 1 above and Formula 2 based on the standard deviation σ and the average copy numbers x, the results are as presented in Table 1 and FIG. 1. The coefficient of variation CV for a copy number having variation according to a Poisson distribution can be obtained from FIG. 1.

$$\sigma = \sqrt{x} \qquad \text{Formula 2}$$

$$CV = \frac{1}{\sqrt{x}} \qquad \text{Formula 3}$$

TABLE 1

| Average copy number x | Coefficient of variation CV |
|---|---|
| 1.00E+00 | 100.00% |
| 1.00E+01 | 31.62% |
| 1.00E+02 | 10.00% |
| 1.00E+03 | 3.16% |
| 1.00E+04 | 1.00% |
| 1.00E+05 | 0.32% |
| 1.00E+06 | 0.10% |
| 1.00E+07 | 0.03% |
| 1.00E+08 | 0.01% |

From the results of Table 1 and FIG. 1, it can be understood that when a well is to be filled with, for example, a copy number of 100 of amplifiable reagents by a serial dilution method, the final copy number of amplifiable reagents to be filled in the reaction solution has a coefficient of variation (CV) of at least 10%, even when other accuracies are ignored.

The device of the present disclosure is based on a finding that the technique described in Japanese Unexamined Patent Application Publication No. 2015-195735 includes a manual operation for fractionating cells into which a target nucleic acid sequence is introduced, one cell by one cell with a manipulator, and hence cannot fill nucleic acid samples at a high accuracy in a wide concentration range of the series of nucleic acid samples.

The device of the present disclosure includes at least two wells, preferably includes an identifier unit and a base material, and further includes other members as needed.

The device of the present disclosure may also be referred to as testing device.

<Well>

For example, the shape, the number, the volume, the material, and the color of the well are not particularly limited and may be appropriately selected depending on the intended purpose.

The shape of the well is not particularly limited and may be appropriately selected depending on the intended purpose so long as an amplifiable reagent can be placed in the well. Examples of the shape of the well include: concaves such as a flat bottom, a round bottom, a U bottom, and a V bottom; and sections on a substrate.

The number of wells is preferably a plural number of 2 or greater, more preferably 5 or greater, and yet more preferably 50 or greater.

Linked microtubes or a multi-well plate with the number of wells of 2 or greater are/is suitably used.

Examples of linked microtubes include 2, 3, 4, 6, 8, 12, 16, 24, or 48 linked-microtubes.

Examples of the multi-well plate include a 24-well, 48-well, 96-well, 384-well, or 1,536-well plate.

The volume of the well is not particularly limited, may be appropriately selected depending on the intended purpose, and is preferably 10 microliters or greater but 1,000 microliters or less in consideration of the amount of a sample used in a common nucleic acid testing device.

The material of the well is not particularly limited and may be appropriately selected depending on the intended purpose. Examples of the material of the well include polystyrene, polypropylene, polyethylene, fluororesins, acrylic resins, polycarbonate, polyurethane, polyvinyl chloride, and polyethylene terephthalate.

Examples of the color of the well include transparent colors, semi-transparent colors, chromatic colors, and complete light-shielding colors.

Wettability of the well is not particularly limited and may be appropriately selected depending on the intended purpose. The wettability of the well is preferably water repellency. When the wettability of the well is water repellency, adsorption of the amplifiable reagent to the internal wall of the well can be reduced. Further, when the wettability of the well is water repellency, the amplifiable reagent, a primer, and an amplifying reagent in the well can be moved in a state of a solution.

The method for imparting water repellency to the internal wall of the well is not particularly limited and may be appropriately selected depending on the intended purpose. Examples of the method include a method of forming a fluororesin coating film, a fluorine plasma treatment, and an embossing treatment. Particularly, by applying a water repellency imparting treatment that imparts a contact angle of 100 degrees or greater, it is possible to suppress reduction of the amplifiable reagent due to spill of the liquid and suppress increase of uncertainty (or coefficient of variation).

<Base Material>

The device is preferably a plate-shaped device obtained by providing a well in a base material, but may be linking-type well tubes such as 8-series tubes.

For example, the material, the shape, the size, and the structure of the base material are not particularly limited and may be appropriately selected depending on the intended purpose.

The material of the base material is not particularly limited and may be appropriately selected depending on the intended purpose. Examples of the material of the base material include semiconductors, ceramics, metals, glass, quartz glass, and plastics. Among these materials, plastics are preferable.

Examples of the plastics include polystyrene, polypropylene, polyethylene, fluororesins, acrylic resins, polycarbonate, polyurethane, polyvinyl chloride, and polyethylene terephthalate.

The shape of the base material is not particularly limited and may be appropriately selected depending on the intended purpose. For example, board shapes and plate shapes are preferable.

The structure of the base material is not particularly limited, may be appropriately selected depending on the intended purpose, and may be, for example, a single-layer structure or a multilayered structure.

<Identifier Unit>

It is preferable that the device include an identifier unit that enables identifying at least any one of information on the coefficient of variation CV of the wells in which the specific copy number of the amplifiable reagent is less than 100, information on the coefficient of variation CV of the wells in which the specific copy number of the amplifiable reagent is 100 or greater, and information on uncertainty of the specific copy number.

The identifier unit is not particularly limited and may be appropriately selected depending on the intended purpose. Examples of the identifier unit include a memory, an IC chip, a barcode, a QR code (registered trademark), a Radio Frequency Identifier (hereinafter may also be referred to as "RFID"), color coding, and printing.

The position at which the identifier unit is provided and the number of identifier units are not particularly limited and may be appropriately selected depending on the intended purpose.

Examples of the information to be stored in the identifier unit include not only the information indicating that the amplifiable reagent is filled in the wells in the specific copy number, but also results of analyses (for example, activity value and emission intensity), the number of amplifiable reagents (for example, the number of cells), whether cells are alive or dead, which of a plurality of wells is filled with the amplifiable reagent, the kind of the amplifiable reagent, the measurement date and time, and the name of the person in charge of measurement.

The information stored in the identifier unit can be read with various kinds of reading units. For example, when the identifier unit is a barcode, a barcode reader is used as the reading unit.

The method for writing information in the identifier unit is not particularly limited and may be appropriately selected depending on the intended purpose. Examples of the method include manual input, a method of directly writing data through a liquid droplet forming device configured to count the number of amplifiable reagents during dispensing of the amplifiable reagents into the wells, transfer of data stored in a server, and transfer of data stored in a cloud system.

<Other Members>

The other members are not particularly limited and may be appropriately selected depending on the intended purpose. Examples of the other members include a sealing member.

—Sealing Member—

It is preferable that the device include a sealing member in order to prevent mixing of foreign matters into the wells and outflow of the filled materials.

It is preferable that the sealing member be configured to be capable of sealing at least one well and separable at a perforation in order to be capable of sealing or opening each one of the wells individually.

The shape of the sealing member is preferably a cap shape matching the inner diameter of a well, or a film shape for covering the well opening.

Examples of the material of the sealing member include polyolefin resins, polyester resins, polystyrene resins, and polyamide resins.

It is preferable that the sealing member have a film shape that can seal all wells at a time. It is also preferable that the sealing member be configured to have different adhesive strengths for wells that need to be reopened and wells that need not, in order that the user can reduce improper use.

The state of the amplifiable reagent, a primer, and an amplifying reagent in the well is not particularly limited and may be appropriately selected depending on the intended purpose. For example, the state of the amplifiable reagent, a primer, and an amplifying reagent may be a state of either a solution or a solid. In terms of convenience of use, the state of the amplifiable reagent, a primer, and an amplifying reagent is particularly preferably a state of a solution. In a state of a solution, a user can use the amplifiable reagent, a primer, and an amplifying reagent for a test immediately. In terms of transportation, the state of the amplifiable reagent, a primer, and an amplifying reagent is particularly preferably a state of a solid and more preferably a dry state. In a solid dry state, a reaction speed at which the amplifiable reagent is decomposed by, for example, a breakdown enzyme, can be reduced, and storage stability of the amplifiable reagent, a primer, and an amplifying reagent can be improved.

It is preferable that the amplifiable reagent, a primer, and an amplifying reagent be filled in appropriate amounts in the device in the solid dry state, in order to make it possible to use the amplifiable reagent, a primer, and an amplifying reagent in the form of a reaction solution immediately by dissolving the amplifiable reagent, a primer, and an amplifying reagent in a buffer or water immediately before use of the device.

The drying method is not particularly limited and may be appropriately selected depending on the intended purpose. Examples of the drying method include freeze drying, heating drying, hot-air drying, vacuum drying, steam drying, suction drying, infrared drying, barrel drying, and spin drying.

In the device of the present disclosure, the amplifiable reagent is contained in a specific copy number in at least two wells.

A copy number means the number of target or specific base sequences in an amplifiable reagent contained in the well.

The target base sequence refers to a base sequence including defined base sequences in at least primer and probe regions. Specifically, a base sequence having a defined total length is also referred to as specific base sequence.

A specific copy number refers to the aforementioned copy number that specifies the number of target base sequences at accuracy of a certain level or higher.

This means that the specific copy number is known as the number of target base sequences actually contained in a well. That is, the specific copy number in the present disclosure is more accurate or reliable as a number than a predetermined copy number (calculated estimated value) obtained according to existing serial dilution methods, and is a controlled value that has no dependency on a Poisson distribution even if the value is within a low copy number region of 1,000 or lower in particular. When it is said that the specific copy number is a controlled value, it is preferable that a coefficient of variation CV expressing uncertainty roughly satisfy either $CV<1/\sqrt{x}$ with respect to an average copy number x or $CV \leq 20\%$. Hence, use of a device including wells in which a target base sequence is contained in the specific copy number makes it possible to perform qualitative or quantitative testing of samples containing the target base sequence more accurately than ever.

When the number of target base sequences and the number of nucleic acid molecules including the sequence coincide with each other, "copy number" and "number of molecules" may be associated with each other.

Specifically, for example, in the case of norovirus, when the number of viruses is 1, the number of nucleic acid molecules is 1 and the copy number is 1. In the case of yeast at a GI phase, when the number of yeast cells is 1, the number of nucleic acid molecules (the number of same chromosomes) is 1 and the copy number is 1. In the case of human cell at a G0/GI phase, when the number of human cells is 1, the number of nucleic acid molecules (the number of same chromosomes) is 2 and the copy number is 2.

Further, in the case of yeast at a GI phase having the target base sequence introduced at two positions, when the number of yeast cells is 1, the number of nucleic acid molecules (the number of same chromosomes) is 1 and the copy number is 2.

In the present disclosure, a specific copy number of the amplifiable reagent may be referred to as absolute number of the amplifiable reagent.

The amplifiable reagent is described in detail below, and a nucleic acid can be suitably used as the amplifiable reagent.

The device includes wells in which the specific copy number of the amplifiable reagent is less than 100, and wells in which the specific copy number of the amplifiable reagent is 100 or greater.

As for the coefficient of variation CV of the wells in which the specific copy number of the amplifiable reagent is less than 100, a formula: $CV<1/\sqrt{x}$, or preferably, $CV<1/2\sqrt{x}$ is established between the coefficient of variation CV for the specific copy number and an average specific copy number x of the amplifiable reagent. Further, regardless of the value taken by the average specific copy number, it is preferable that the coefficient of variation CV of the wells in which the specific copy number of the amplifiable reagent is less than 100 be 20% or lower, or more preferably 10% or lower. In this range, it is possible to fill the amplifiable reagent at a high accuracy, when the specific copy number is less than 100.

It is preferable that the coefficient of variation CV of the wells in which the specific copy number of the amplifiable reagent is 100 or greater be 20% or lower. In this range, it is possible to fill the amplifiable reagent at a high accuracy, when the specific copy number is 100 or greater.

Here, the coefficient of variation is a value obtained by dividing standard deviation σ by an average specific copy number x. A term "CV value" is used as abbreviation. The coefficient of variation CV for a specific copy number can be obtained from FIG. 1.

For the specific copy number of the amplifiable reagent of less than 100, it is preferable that a formula: $CV<1/\sqrt{x}$ be established between the coefficient of variation CV for the specific copy number and the average specific copy number x of the amplifiable reagent.

It is preferable that the coefficient of variation CV of the wells in which the specific copy number of the amplifiable reagent is 100 or greater be 20% or lower.

Figure 2:
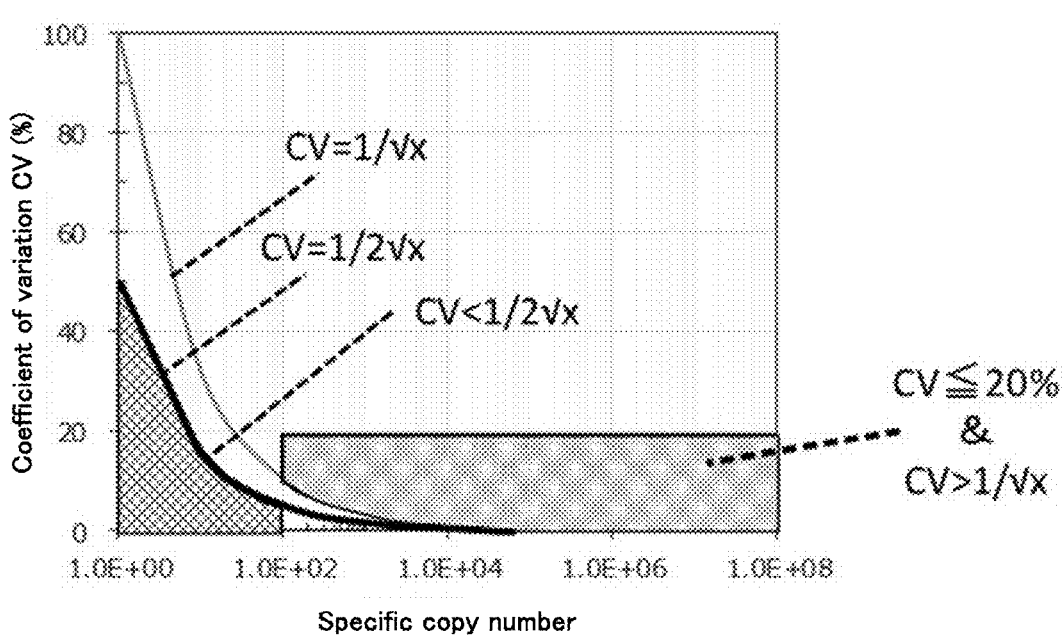
FIG. 2 is a graph plotting a relationship between an average specific copy number x and a coefficient of variation CV, for a case where the specific copy number is less than 100 and a case where the specific copy number is 100 or greater.

As a result, the device satisfies the relationship plotted in FIG. 2.

FIG. 2 is a graph plotting the relationship between the specific copy number (the copy number of nucleic acids filled in a well) and the coefficient of variation. FIG. 2 presents the following relational expressions: $CV=1/\sqrt{x}$ and $CV=\frac{1}{2}\sqrt{x}$, between the average specific copy number x and the coefficient of variation CV, a specific copy number of 100, and a CV value of 20%. From FIG. 2, it is possible to know (1) a region in which the specific copy number of the amplifiable reagent is less than 100, and a formula: $CV<1/\sqrt{x}$ is established between the coefficient of variation CV for that specific copy number and the average specific copy number x of the amplifiable reagent, and (2) a region in which the average specific copy number of the amplifiable reagent is 100 or greater, a formula: $CV>1/\sqrt{x}$ is established between the coefficient of variation CV for that specific copy number and the average specific copy number x of the amplifiable reagent, and $CV\leq20\%$ is established. Hence, the device enables a highly accurate measurement in a wide range varying from a low copy number to a high copy number.

It is preferable that the number of wells be 2 or greater, and that the specific copy number of the amplifiable reagent in one well and the specific copy number of the amplifiable reagent in any other well be of two or more levels different from each other. Examples of a combination of specific copy numbers include a combination of 1, 2, 3, 4, 5, 6, 7, 8, 9, and 10, a combination of 1, 3, 5, 7, and 9, and a combination of 2, 4, 6, 8, and 10.

It is preferable that the number of wells be 2 or greater, that the specific copy number of the amplifiable reagent in one well be $10^{N1}$, and that the specific copy number of the amplifiable reagent in any other well be $10^{N2}$ (where N1 and N2 are continuous integers). Examples of a combination of specific copy numbers for such a case include a combination of 1, 10, 100, and 1,000, and a combination of 100, 1,000, 10,000, 100,000, and 1,000,000. Hence, the device enables easy generation of a calibration curve for a wide range varying from a low copy number to a high copy number.

It is preferable that for a specific copy number of the amplifiable reagent in a well, the device further include information on uncertainty of the specific copy number.

"Uncertainty" is defined in ISO/IEC Guide 99:2007 [International Vocabulary of Metrology-Basics and general concepts and related terms (VIM)] as "a parameter that characterizes measurement result-incidental variation or dispersion of values rationally linkable to the measured quantity".

Here, "values rationally linkable to the measured quantity" means candidates for the true value of the measured quantity. That is, uncertainty means information on the variation of the results of measurement due to operations and devices involved in production of a measurement target. With a greater uncertainty, a greater variation is predicted in the results of measurement.

For example, the uncertainty may be standard deviation obtained from the results of measurement, or a half value of a reliability level, which is expressed as a numerical range in which the true value is contained at a predetermined probability or higher.

The uncertainty may be calculated according to the methods based on, for example, Guide to the Expression of Uncertainty in Measurement (GUM: ISO/IEC Guide 98-3), and Japan Accreditation Board Note 10, Guideline on Uncertainty in Measurement in Test. As the method for calculating the uncertainty, for example, there are two types of applicable methods: a type-A evaluation method using, for example, statistics of the measured values, and a type-B evaluation method using information on uncertainty obtained from, for example, calibration certificate, manufacturer's specification, and information open to the public.

All uncertainties due to factors such as operations and measurement can be expressed by the same reliability level, by conversion of the uncertainties to standard uncertainty. Standard uncertainty indicates variation in the average value of measured values.

In an example method for calculating the uncertainty, for example, factors that may cause uncertainties are extracted, and uncertainties (standard deviations) due to the respective factors are calculated. Then, the calculated uncertainties due to the respective factors are synthesized according to the sum-of-squares method, to calculate a synthesized standard uncertainty. In the calculation of the synthesized standard uncertainty, the sum-of-squares method is used. Therefore, a factor that causes a sufficiently small uncertainty can be ignored, among the factors that cause uncertainties. As the uncertainty, a coefficient of variation (CV) obtained by dividing a synthesized standard uncertainty by an expected value.

It is desirable to appropriately calculate the uncertainty to be associated with each well, by the filling method or the producing method based on serial dilution described above.

As information on the uncertainty of a specific copy number of the amplifiable reagent, all factors involved in production of the device may be taken into consideration. Examples of the information include information on the factors presented below.

For example, in a production process of introducing the intended amplifiable reagent into cells and dispensing the cells while counting the number of cells, examples of the factors of uncertainties when the specific copy number of the amplifiable reagent is less than 100 include the number of amplifiable reagents in a cell, the unit configured to locate the cells in the device (including any outcomes of operations of an inkjet device or each section of the device, such as operation timings of the device), the frequency at which cells are located at appropriate positions of the device, and contamination due to destruction of cells in a cell suspension and consequent mixing of the amplifiable reagent into the cell suspension (hereinafter may also be described as mixing of contaminants).

Examples of the factors of uncertainties when the specific copy number of the amplifiable reagent is 100 or greater include the copy number of amplifiable reagents, the densities of a diluent solvent and an amplifiable reagent solution, the operation of an electronic balance during weight measurement, uncertainty based on a Poisson distribution, and a pipetting operation during filling of the amplifiable reagent.

It is preferable that a well contain at least any one of a primer and an amplifying reagent.

A primer is a synthetic oligonucleotide having a complementary base sequence that includes from 18 through 30 bases and is specific to a template DNA of a polymerase chain reaction (PCR). A pair of primers, namely a forward primer and a reverse primer, are set at two positions in a manner to sandwich the region to be amplified.

Examples of the amplifying reagent for a polymerase chain reaction (PCR) include enzymes such as DNA polymerase, matrices such as the four kinds of bases (dGTP, dCTP, dATP, and dTTP), $Mg^{2+}$ (2 mM magnesium chloride), and a buffer for maintaining the optimum pH (pH of from 7.5 through 9.5).

It is preferable that the device include a negative control well in which the copy number of amplifiable reagents is zero and a positive control well in which the copy number of amplifiable reagents is 10 or greater.

Detection sensed in the negative control and non-detection sensed in the positive control suggest abnormality of the detection system (the reagent or the device). With the negative control and the positive control, the user can immediately recognize a problem when the problem occurs, and can stop the measurement and inspect the root of the problem.

It is preferable that the amplifiable reagent be a nucleic acid. It is preferable that the nucleic acid be incorporated into the nucleus of a cell.

—Nucleic Acid—

A nucleic acid means a polymeric organic compound in which a nitrogen-containing base derived from purine or pyrimidine, sugar, and phosphoric acid are bonded with one another regularly. Examples of the nucleic acid also include a fragment of a nucleic acid or an analog of a nucleic acid or of a fragment of a nucleic acid.

The nucleic acid is not particularly limited and may be appropriately selected depending on the intended purpose. Examples of the nucleic acid include DNA, RNA, and cDNA.

The nucleic acid or nucleic acid fragment may be a natural product obtained from a living thing, or a processed product of the natural product, or a product produced by utilizing a genetic recombination technique, or chemically synthesized artificially synthesized nucleic acid. One of these nucleic acids may be used alone or two or more of these nucleic acids may be used in combination. With artificially synthesized nucleic acids, it is possible to suppress impurities and reduce the number of molecules. This makes it possible to improve the initial reaction efficiency.

An artificially synthesized nucleic acid means an artificially synthesized nucleic acid produced to have the same constituent components (base, deoxyribose, and phosphoric acid) as naturally existent DNA or RNA. Examples of the artificially synthesized nucleic acid include not only a nucleic acid having a base sequence coding a protein, but also a nucleic acid having an arbitrary base sequence.

Examples of the analog of a nucleic acid or a nucleic acid fragment include a nucleic acid or a nucleic acid fragment bonded with a non-nucleic acid component, a nucleic acid or a nucleic acid fragment labeled with a labeling agent such as a fluorescent dye or an isotope (e.g., a primer or a probe labeled with a fluorescent dye or a radioisotope), and an artificial nucleic acid, which is a nucleic acid or a nucleic acid fragment in which the chemical structure of some of the constituent nucleotides is changed (e.g., PNA, BNA, and LNA).

The form of the nucleic acid is not particularly limited and may be appropriately selected depending on the intended purpose. Examples of the form of the nucleic acid include double-strand nucleic acid, single-strand nucleic acid, and partially double-strand or single-strand nucleic acid. Cyclic or straight-chain plasmids can also be used.

The nucleic acid may be modified or mutated.

It is preferable that the nucleic acid have a specific base sequence. The term "specific" means "particularly specified".

The specific base sequence is not particularly limited and may be appropriately selected depending on the intended purpose. Examples of the specific base sequence include base sequences used for infectious disease testing, naturally non-existent non-natural base sequences, animal cell-derived base sequences, plant cell-derived base sequences, fungal cell-derived base sequences, bacterium-derived base sequences, and virus-derived base sequences. One of these base sequences may be used alone or two or more of these base sequences may be used in combination.

When using a non-natural base sequence, the specific base sequence preferably has a GC content of 30% or higher but 70% or lower, and preferably has a constant GC content (for example, see SEQ NO. 1).

The base length of the specific base sequence is not particularly limited, may be appropriately selected depending on the intended purpose, and may be, for example, a base length of 20 base pairs (or mer) or longer but 10,000 base pairs (or mer) or shorter.

When using a base sequence used for infectious disease testing, the base sequence is not particularly limited and may be appropriately selected depending on the intended purpose so long as the base sequence includes a base sequence specific to the intended infectious disease. It is preferable that the base sequence include a base sequence designated in official analytical methods or officially announced methods (for example, see SEQ NOS. 2 and 3).

The nucleic acid may be a nucleic acid derived from the cells to be used, or a nucleic acid introduced by transgenesis. When a nucleic acid introduced by transgenesis and a plasmid are used as the nucleic acid, it is preferable to confirm that one copy of the nucleic acid is introduced per cell. The method for confirming that one copy of the nucleic acid is introduced is not particularly limited and may be appropriately selected depending on the intended purpose. Examples of the method include a sequencer, a PCR method, and a Southern blotting method.

One kind or two or more kinds of nucleic acids having specific base sequences may be introduced by transgenesis. Also in the case of introducing only one kind of a nucleic acid by transgenesis, base sequences of the same kind may be introduced in tandem depending on the intended purpose.

The method for transgenesis is not particularly limited and may be appropriately selected depending on the intended purpose so long as the method can introduce an intended copy number of specific nucleic acid sequences at an intended position. Examples of the method include homologous recombination, CRISPR/Cas9, CRISPR/Cpf1, TALEN, Zinc finger nuclease, Flip-in, and Jump-in. In the case of yeast fungi, homologous recombination is preferable among these methods in terms of a high efficiency and ease of controlling.

—Carrier—

It is preferable to handle the amplifiable reagent in a state of being carried on a carrier. When the amplifiable reagent is a nucleic acid, a preferable form is the nucleic acid being carried (or more preferably encapsulated) by the carrier having a particle shape (carrier particles).

The carrier is not particularly limited and may be appropriately selected depending on the intended purpose. Examples of the carrier include a cell, a resin, liposome, and microcapsule.

—Cells—

A cell means a structural, functional unit that includes an amplifiable reagent (for example, a nucleic acid) and forms an organism.

The cells are not particularly limited and may be appropriately selected depending on the intended purpose. All kinds of cells can be used regardless of whether the cells are eukaryotic cells, prokaryotic cells, multicellular organism cells, and unicellular organism cells. One of these kinds of cells may be used alone or two or more of these kinds of cells may be used in combination.

The eukaryotic cells are not particularly limited and may be appropriately selected depending on the intended purpose. Examples of the eukaryotic cells include animal cells, insect cells, plant cells, fungi, algae, and protozoans. One of these kinds of eukaryotic cells may be used alone or two or more of these kinds of eukaryotic cells may be used in combination. Among these eukaryotic cells, animal cells and fungi are preferable.

Adherent cells may be primary cells directly taken from tissues or organs, or may be cells obtained by passaging primary cells directly taken from tissues or organs a few times. Adherent cells may be appropriately selected depending on the intended purpose. Examples of adherent cells include differentiated cells and undifferentiated cells.

Differentiated cells are not particularly limited and may be appropriately selected depending on the intended purpose. Examples of differentiated cells include: hepatocytes, which are parenchymal cells of a liver; stellate cells; Kupffer cells; endothelial cells such as vascular endothelial cells, sinusoidal endothelial cells, and corneal endothelial cells; fibroblasts; osteoblasts; osteoclasts; periodontal ligament-derived cells; epidermal cells such as epidermal keratinocytes; epithelial cells such as tracheal epithelial cells, intestinal epithelial cells, cervical epithelial cells, and corneal epithelial cells; mammary glandular cells; pericytes; muscle cells such as smooth muscle cells and myocardial cells; renal cells; pancreatic islet cells; nerve cells such as peripheral nerve cells and optic nerve cells; chondrocytes; and bone cells.

Undifferentiated cells are not particularly limited and may be appropriately selected depending on the intended purpose. Examples of undifferentiated cells include: pluripotent stem cells such as embryotic stem cells, which are undifferentiated cells, and mesenchymal stem cells having pluripotency; unipotent stem cells such as vascular endothelial progenitor cells having unipotency; and iPS cells.

Fungi are not particularly limited and may be appropriately selected depending on the intended purpose. Examples of fungi include molds and yeast fungi. One of these kinds of fungi may be used alone or two or more of these kinds of fungi may be used in combination. Among these kinds of fungi, yeast fungi are preferable because the cell cycles are adjustable and monoploids can be used.

The cell cycle means a cell proliferation process in which cells undergo cell division and cells (daughter cells) generated by the cell division become cells (mother cells) that undergo another cell division to generate new daughter cells.

Yeast fungi are not particularly limited and may be appropriately selected depending on the intended purpose. For example, yeast fungi that are synchronously cultured to synchronize at a G0/G1 phase, and fixed at a G1 phase are preferable.

Further, for example, as yeast fungi, Bar1-deficient yeasts with enhanced sensitivity to a pheromone (sex hormone) that controls the cell cycle at a G1 phase are preferable. When yeast fungi are Bar1-deficient yeasts, the abundance ratio of yeast fungi with uncontrolled cell cycles can be reduced. This makes it possible to, for example, prevent a specific nucleic acid from increasing in number in the cells contained in a well.

The prokaryotic cells are not particularly limited and may be appropriately selected depending on the intended purpose. Examples of the prokaryotic cells include eubacteria and archaea. One of these kinds of prokaryotic cells may be used alone or two or more of these kinds of prokaryotic cells may be used in combination.

As the cells, dead cells are preferable. With dead cells, it is possible to prevent occurrence of cell division after fractionation.

As the cells, cells that can emit light upon reception of light are preferable. With cells that can emit light upon reception of light, it is possible to land the cells into wells while having a highly accurate control on the number of cells.

Reception of light means receiving of light.

An optical sensor means a passive sensor configured to collect, with a lens, any light in the range from visible light rays visible by human eyes to near infrared rays, short-wavelength infrared rays, and thermal infrared rays that have longer wavelengths than the visible light rays, to obtain, for example, shapes of target cells in the form of image data.

—Cells that can Emit Light Upon Reception of Light—

The cells that can emit light upon reception of light are not particularly limited and may be appropriately selected depending on the intended purpose so long as the cells can emit light upon reception of light. Examples of the cells include cells stained with a fluorescent dye, cells expressing a fluorescent protein, and cells labeled with a fluorescent-labeled antibody.

A cellular site stained with a fluorescent dye, expressing a fluorescent protein, or labeled with a fluorescent-labeled antibody is not particularly limited. Examples of the cellular site include a whole cell, a cell nucleus, and a cellular membrane.

—Fluorescent Dye—

Examples of the fluorescent dye include fluoresceins, azo dyes, rhodamines, coumarins, pyrenes, cyanines. One of these fluorescent dyes may be used alone or two or more of these fluorescent dyes may be used in combination. Among these fluorescent dyes, fluoresceins, azo dyes, rhodamines, and cyanines are preferable, and eosin, Evans blue, trypan blue, rhodamine 6G, rhodamine B, rhodamine 123, and Cy3 are more preferable.

As the fluorescent dye, a commercially available product may be used. Examples of the commercially available product include product name: EOSIN Y (available from Wako Pure Chemical Industries, Ltd.), product name: EVANS BLUE (available from Wako Pure Chemical Industries, Ltd.), product name: TRYPAN BLUE (available from Wako Pure Chemical Industries, Ltd.), product name: RHODAMINE 6G (available from Wako Pure Chemical Industries, Ltd.), product name: RHODAMINE B (available from Wako Pure Chemical Industries, Ltd.), and product name: RHODAMINE 123 (available from Wako Pure Chemical Industries, Ltd.).

—Fluorescent Protein—

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. One of these fluorescent proteins may be used alone or two or more of these fluorescent proteins may be used in combination.

—Fluorescent-Labeled Antibody—

The fluorescent-labeled antibody is not particularly limited and may be appropriately selected depending on the intended purpose so long as the fluorescent-labeled antibody is fluorescent-labeled. Examples of the fluorescent-labeled antibody include CD4-FITC and CD8-PE. One of these fluorescent-labeled antibodies may be used alone or two or more of these fluorescent-labeled antibodies may be used in combination.

The volume average particle diameter of the cells is preferably 30 micrometers or less, more preferably 10 micrometers or less, and particularly preferably 7 micrometers or less in a free state. When the volume average particle diameter of the cells is 30 micrometers or less, the cells can be suitably used in an inkjet method or a liquid droplet discharging unit such as a cell sorter.

The volume average particle diameter of the cells can be measured by, for example, a measuring method described below.

Ten microliters is extracted from a produced stained yeast dispersion liquid and poured onto a plastic slide formed of PMMA. Then, with an automated cell counter (product name: COUNTESS AUTOMATED CELL COUNTER, available from Invitrogen), the volume average particle diameter of the cells can be measured. The cell number can be obtained by a similar measuring method.

The concentration of the cells in a cell suspension is not particularly limited, may be appropriately selected depending on the intended purpose, and is preferably $5 \times 10^4$ cells/mL or higher but $5 \times 10^8$ cells/mL or lower and more preferably $5 \times 10^4$ cells/mL or higher but $5 \times 10^7$ cells/mL or lower. When the cell number is $5 \times 10^4$ cells/mL or higher but $5 \times 10^8$ cells/mL or lower, it can be ensured that cells be contained in a discharged liquid droplet without fail. The cell number can be measured with an automated cell counter (product name: COUNTESS AUTOMATED CELL COUNTER, available from Invitrogen) in the same manner as measuring the volume average particle diameter.

The cell number of cells including a nucleic acid is not particularly limited and may be appropriately selected depending on the intended purpose so long as the cell number is a plural number.

—Resin—

The material, the shape, the size, and the structure of the resin are not particularly limited and may be appropriately selected depending on the intended purpose so long as the resin can carry the amplifiable reagent (for example, a nucleic acid).

—Liposome—

A liposome is a lipid vesicle formed of a lipid bilayer containing lipid molecules. Specifically, the liposome means a lipid-containing closed vesicle including a space separated from the external environment by a lipid bilayer produced based on the polarities of a hydrophobic group and a hydrophilic group of lipid molecules.

The liposome is a closed vesicle formed of a lipid bilayer using a lipid, and contains an aqueous phase (internal aqueous phase) in the space in the closed vesicle. The internal aqueous phase contains, for example, water. The liposome may be single-lamellar (single-layer lamellar or unilamellar with a single bilayer) or multilayer lamellar (multilamellar, with an onion-like structure including multiple bilayers, with the individual layers separated by watery layers).

As the liposome, a liposome that can encapsulate an amplifiable reagent (for example, a nucleic acid) is preferable. The form of encapsulation is not particularly limited. "Encapsulation" means a form of a nucleic acid being contained in the internal aqueous phase and the layer of the liposome. Examples of the form include a form of encapsulating a nucleic acid in the closed space formed of the layer, a form of encapsulating a nucleic acid in the layer per se, and a combination of these forms.

The size (average particle diameter) of the liposome is not particularly limited so long as the liposome can encapsulate an amplifiable reagent (for example, a nucleic acid). It is preferable that the liposome have a spherical form or a form close to the spherical form.

The component (layer component) constituting the lipid bilayer of the liposome is selected from lipids. As the lipid, an arbitrary lipid that can dissolve in a mixture solvent of a water-soluble organic solvent and an ester-based organic solvent can be used. Specific examples of the lipid include phospholipids, lipids other than phospholipids, cholesterols, and derivatives of these lipids. These components may be formed of a single kind of a component or a plurality of kinds of components.

—Microcapsule—

A microcapsule means a minute particle having a wall material and a hollow structure, and can encapsulate an amplifiable reagent (for example, a nucleic acid) in the hollow structure.

The microcapsule is not particularly limited, and, for example, the wall material and the size of the microcapsule may be appropriately selected depending on the intended purpose.

Examples of the wall material of the microcapsule include polyurethane resins, polyurea, polyurea-polyurethane resins, urea-formaldehyde resins, melamine-formaldehyde resins, polyamide, polyester, polysulfone amide, polycarbonate, polysulfinate, epoxyr, acrylic acid ester, methacrylic acid ester, vinyl acetate, and gelatin. One of these wall materials may be used alone or two or more of these wall materials may be used in combination.

The size of the microcapsule is not particularly limited and may be appropriately selected depending on the intended purpose so long as the microcapsule can encapsulate an amplifiable reagent (for example, a nucleic acid).

The method for producing the microcapsule is not particularly limited and may be appropriately selected depending on the intended purpose. Examples of the method include an in-situ method, an interfacial polymerization method, and a coacervation method.

Figure 3:
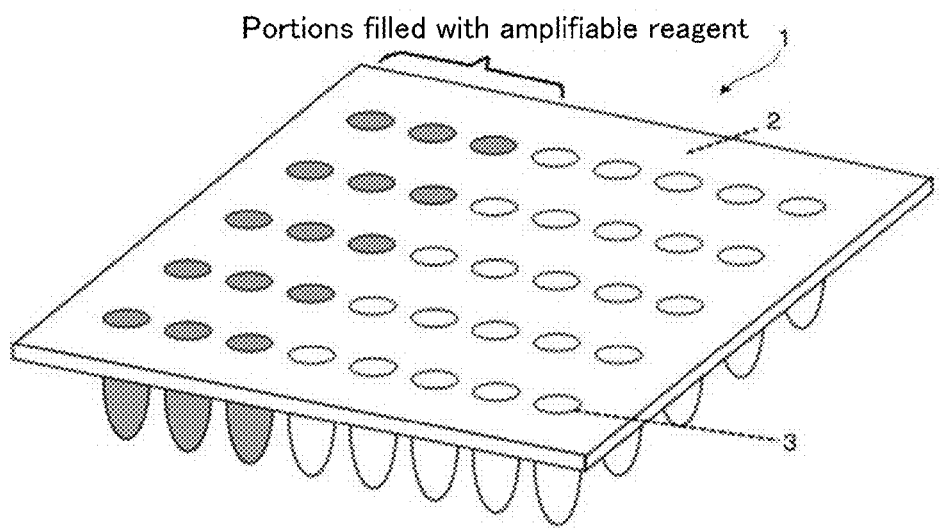
FIG. 3 is a perspective view illustrating an example of a device of the present disclosure.
Figure 4:
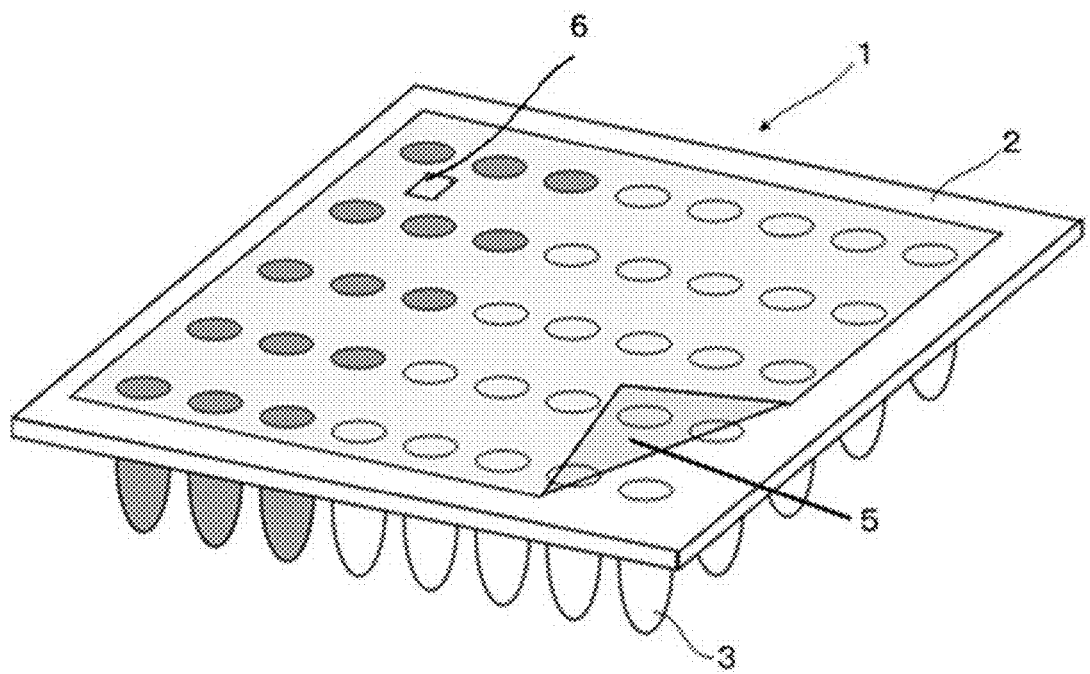
FIG. 4 is a perspective view illustrating another example of a device of the present disclosure.
Figure 5:
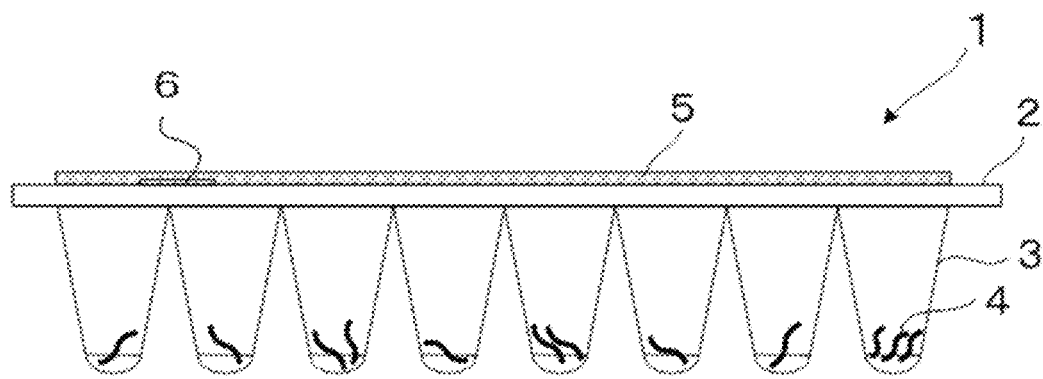
FIG. 5 is a side view of FIG. 4.

Here, FIG. 3 is a perspective view illustrating an example of the device of the present disclosure. FIG. 4 is a perspective view illustrating another example of the device of the present disclosure. FIG. 5 is a side view of the device of FIG. 4. In the device 1, a plurality of wells 3 are provided in a base material 2, and a nucleic acid 4 serving as the amplifiable reagent is filled in specific copy numbers in the wells 3. In FIG. 4 and FIG. 5, the reference sign 5 denotes a sealing member.

For example, as illustrated in FIG. 4 and FIG. 5, an IC chip or a barcode (identifier unit 6) storing the information on the specific copy number of the reagent filled in each well 3 and the uncertainty (or certainty) of the specific copy number, or information related with these kinds of information is placed at a position that is between the sealing member 5 and the base material 2 and does not overlap the openings of the wells. This is suitable for preventing, for example, unintentional alteration of the identifier unit 6.

With the identifier unit, the device can be distinguished from a common well plate that does not have an identifier unit. Therefore, confusion or mistake can be prevented.

It is preferable that the device 1 also include information on the number of the amplifiable reagent (for example, a nucleic acid) and the uncertainty of the number.

In a case where information on the specific copy number of the amplifiable reagent in the device 1 and the uncertainty of the specific copy number is stored in a memory unit of a server of a network such as a cloud system, the information stored in the identifier unit 6 of the device 1 may be information uniquely associated with the information in the cloud system.

Information is obtained from the memory unit of the server of the remote network, based on the unique information in the identifier unit.

A recognition unit may be provided on the device 1 per se, or may be provided as an attachment of the device. The combination of the device 1 and the recognition unit as the attachment may be provided as a testing kit.

Information associating the information on the absolute number of the amplifiable reagent and the uncertainty of the absolute number with a container is identifiable. This enables association of the container in which a nucleic acid having a specific base sequence is contained in a known copy number, during calibration or quality assurance of an analytical test or an analyzing device.

Figure 6:
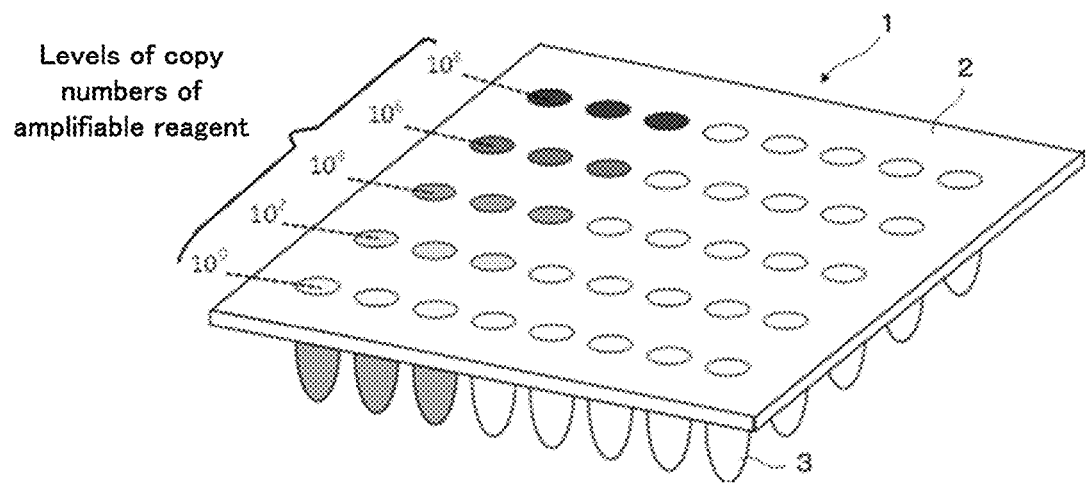
FIG. 6 is a perspective view illustrating another example of a device of the present disclosure.

FIG. 6 is a perspective view illustrating another example of the device of the present disclosure. In the device of FIG. 6, levels of the copy number of the amplifiable reagent include the following five levels: $10^0$, $10^2$, $10^4$, $10^6$, and $10^8$.

FIG. 7 is a diagram illustrating an example of the positions of the wells to be filled with the amplifiable reagent in the device of the present disclosure. The numerals in the wells in FIG. 7 indicate the specific copy numbers of the amplifiable reagent. There are provided wells in which the specific copy number is less than 100, namely 1, 2, 3, 10, and 50, and wells in which the specific copy number is 100 or greater, namely $10^2$, $10^3$, $10^4$, $10^5$, and $10^6$. The wells with no numerals in FIG. 7 are wells for a sample or control measurement.

FIG. 8 is a diagram illustrating another example of the positions of the wells to be filled with the amplifiable reagent in the device of the present disclosure. The numerals in the wells in FIG. 8 indicate the specific copy numbers of the amplifiable reagent. There are provided wells in which the specific copy number is less than 100, namely 1, 3, 5, 10, and 50, and wells in which the specific copy number is 100 or greater, namely $10^2$, $10^3$, $10^4$, $10^5$, and $10^6$. The wells with no numerals in FIG. 8 are wells for a sample or control measurement.

<Method for Producing Device>

The method for producing a device includes "Preparation of amplifiable reagent by diluting method" and "Preparation of amplifiable reagent by discharging method". Both may be performed simultaneously or separately in order in one plate.

<<Preparation of Amplifiable Reagent by Diluting Method>>

It is preferable to prepare the amplifiable reagent by a diluting method when the specific copy number of the amplifiable reagent in one well is 100 or greater. In this case, the specific copy number of the amplifiable reagent is 100 or greater and preferably from 100 through $10^{10}$.

Examples of the diluting method include a method of producing serial dilutions according to a sample preparing method.

Examples of the sample preparing method include a manual operation using a pipette, a micropipetter (available from Eppendorf AG), and a pipetman (available from Eppendorf AG).

<<Preparation of Amplifiable Reagent by Discharging Method>>

It is preferable to prepare the amplifiable reagent by a discharging method when the specific copy number of the amplifiable reagent in one well is less than 100. In this case, the specific copy number of the amplifiable reagent is less than 100, preferably 50 or less, more preferably 10 or less, and yet more preferably 5 or less.

Examples of the discharging method include an inkjet discharging method, a cell sorter, and a flow cytometer.

A method for producing a device by a discharging method, using cells in which a specific nucleic acid as the amplifiable reagent is contained in a specific copy number of less than 100 will be described in detail below.

The method for producing a device includes a cell suspension preparing step of preparing a cell suspension containing a plurality of cells including a specific nucleic acid and a solvent, a liquid droplet landing step of discharging the cell suspension in the form of liquid droplets to sequentially land the liquid droplets in wells of a plate, a cell number counting step of counting the number of cells contained in the liquid droplets with a sensor after the liquid droplets are discharged and before the liquid droplets land in the wells, and a nucleic acid extracting step of extracting nucleic acids from cells in the wells, preferably includes a step of calculating the degree of certainty of an estimated number of nucleic acids in the cell suspension preparing step, the liquid droplet landing step, and the cell number counting step, an outputting step, and a recording step, and further includes other steps as needed.

<<<Cell Suspension Preparing Step>>>

The cell suspension preparing step is a step of preparing a cell suspension containing a plurality of cells including a specific nucleic acid and a solvent.

The solvent means a liquid used for dispersing cells.

Suspension in the cell suspension means a state of cells being present dispersedly in the solvent.

Preparing means a producing operation.

—Cell Suspension—

The cell suspension contains a plurality of cells including a specific nucleic acid and a solvent, preferably contains an additive, and further contains other components as needed.

The plurality of cells including a specific nucleic acid are as described above.

—Solvent—

The solvent is not particularly limited and may be appropriately selected depending on the intended purpose. Examples of the solvent include water, a culture fluid, a separation liquid, a diluent, a buffer, an organic matter dissolving liquid, an organic solvent, a polymeric gel solution, a colloid dispersion liquid, an electrolytic aqueous solution, an inorganic salt aqueous solution, a metal aqueous solution, and mixture liquids of these liquids. One of these solvents may be used alone or two or more of these solvents may be used in combination. Among these solvents, water and a buffer are preferable, and water, a phosphate buffered saline (PBS), and a Tris-EDTA buffer (TE) are more preferable.

—Additive—

An additive is not particularly limited and may be appropriately selected depending on the intended purpose. Examples of the additive include a surfactant, a nucleic acid, and a resin. One of these additives may be used alone or two or more of these additives may be used in combination.

The surfactant can prevent mutual aggregation of cells and improve continuous discharging stability.

The surfactant is not particularly limited and may be appropriately selected depending on the intended purpose. Examples of the surfactant include ionic surfactants and nonionic surfactants. One of these surfactants may be used alone or two or more of these surfactants may be used in combination. Among these surfactants, nonionic surfactants are preferable because proteins are neither modified nor deactivated by nonionic surfactants, although depending on the addition amount of the nonionic surfactants.

Examples of the ionic surfactants include fatty acid sodium, fatty acid potassium, alpha-sulfo fatty acid ester sodium, sodium straight-chain alkyl benzene sulfonate, alkyl sulfuric acid ester sodium, alkyl ether sulfuric acid ester sodium, and sodium alpha-olefin sulfonate. One of these ionic surfactants may be used alone or two or more of these ionic surfactants may be used in combination. Among these ionic surfactants, fatty acid sodium is preferable and sodium dodecyl sulfonate (SDS) is more preferable.

Examples of the nonionic surfactants include alkyl glycoside, alkyl polyoxyethylene ether (e.g., BRIJ series), octyl phenol ethoxylate (e.g., TRITON X series, IGEPAL CA series, NONIDET P series, and NIKKOL OP series), polysorbates (e.g., TWEEN series such as TWEEN 20), sorbitan fatty acid esters, polyoxyethylene fatty acid esters, alkyl maltoside, sucrose fatty acid esters, glycoside fatty acid esters, glycerin fatty acid esters, propylene glycol fatty acid esters, and fatty acid monoglyceride. One of these nonionic surfactants may be used alone or two or more of these nonionic surfactants may be used in combination. Among these nonionic surfactants, polysorbates are preferable.

The content of the surfactant is not particularly limited, may be appropriately selected depending on the intended purpose, and is preferably 0.001% by mass or greater but 30% by mass or less relative to the total amount of the cell suspension. When the content of the surfactant is 0.001% by mass or greater, an effect of adding the surfactant can be obtained. When the content of the surfactant is 30% by mass or less, aggregation of cells can be suppressed, making it possible to strictly control the copy number of nucleic acids in the cell suspension.

The nucleic acid is not particularly limited and may be appropriately selected depending on the intended purpose so long as the nucleic acid does not affect detection of the detection target nucleic acid. Examples of the nucleic acid include ColE1 DNA. With such a nucleic acid, it is possible to prevent the nucleic acid having a target base sequence from adhering to the wall surface of a well.

The resin is not particularly limited and may be appropriately selected depending on the intended purpose. Examples of the resin include polyethyleneimine.

—Other Materials—

Other materials are not particularly limited and may be appropriately selected depending on the intended purpose. Examples of the other materials include a cross-linking agent, a pH adjustor, an antiseptic, an antioxidant, an osmotic pressure regulator, a humectant, and a dispersant.

[Method for Dispersing Cells]

The method for dispersing the cells is not particularly limited and may be appropriately selected depending on the intended purpose. Examples of the method include a medium method such as a bead mill, an ultrasonic method such as an ultrasonic homogenizer, and a method using a pressure difference such as a French press. One of these methods may be used alone or two or more of these methods may be used in combination. Among these methods, the ultrasonic method is more preferable because the ultrasonic method has low damage on the cells. With the medium method, a high crushing force may destroy cellular membranes or cell walls, and the medium may mix as contamination.

[Method for Screening Cells]

The method for screening the cells is not particularly limited and may be appropriately selected depending on the intended purpose. Examples of the method include screening by wet classification, a cell sorter, and a filter. One of these methods may be used alone or two or more of these methods may be used in combination. Among these methods, screening by a cell sorter and a filter is preferable because the method has low damage on the cells.

It is preferable to estimate the number of nucleic acids having a target base sequence from the cell number contained in the cell suspension, by measuring the cell cycles of the cells.

Measuring the cell cycles means quantifying the cell number due to cell division.

Estimating the number of nucleic acids means obtaining the copy number of nucleic acids based on the cell number.

What is to be counted needs not be the cell number, but may be the number of target base sequences. Typically, it is safe to consider that the number of target base sequences is equal to the cell number, because the cells to be selected as the cells to be counted are cells each including one target base sequence (=one target base sequence per cell), or because one target base sequence is introduced per cell by gene recombination. However, nucleic acid replication occurs in cells in order for the cells to undergo cell division at specific cycles. Cell cycles are different depending on the kinds of cells. By extracting a predetermined amount of the solution from the cell suspension and measuring the cycles of a plurality of cells, it is possible to calculate an expected value of the number of target base sequences included in one cell and the degree of certainty of the estimated value. This can be realized by, for example, observing nuclear stained cells with a flow cytometer.

Degree of certainty means a probability of occurrence of one specific event, predicted beforehand, when there are possibilities of occurrence of some events.

Calculation means deriving a needed value by a calculating operation.

Figure 9:
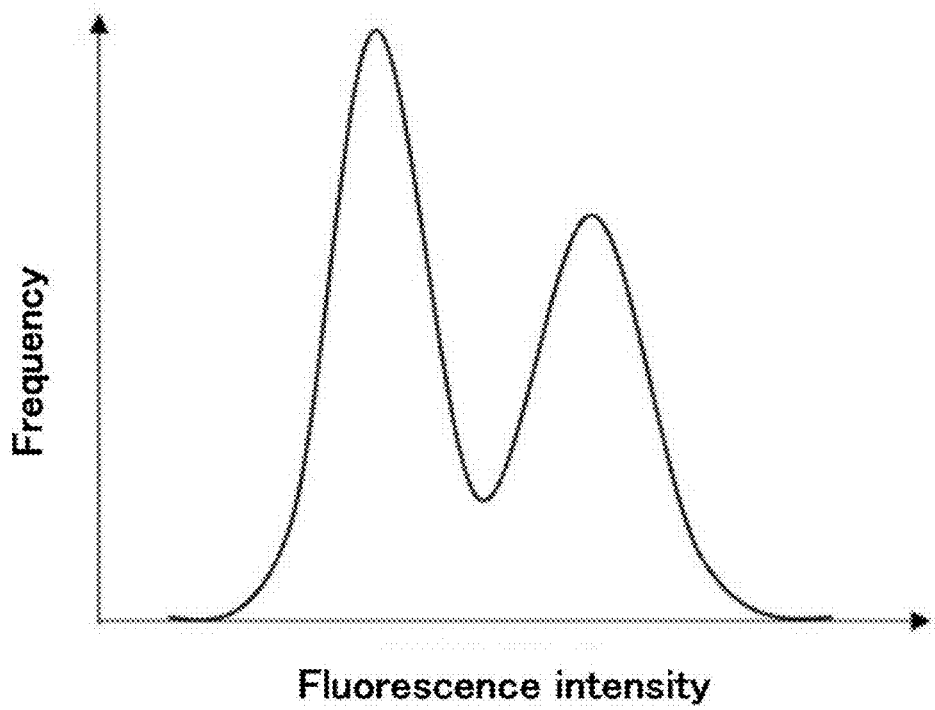
FIG. 9 is a graph plotting an example of a relationship between the frequency and the fluorescence intensity of cells in which DNA replication has occurred.

FIG. 9 is a graph plotting an example of a relationship between the frequency and the fluorescence intensity of cells in which DNA replication has occurred. As plotted in FIG. 9, based on presence or absence of target base sequence replication, two peaks appear on the histogram. Hence, the percentage of presence of cells in which target base sequence replication has occurred can be calculated. Based on this calculation result, the average target base sequence number included in one cell can be calculated. The estimated number of target base sequences can be calculated by multiplying the counted cell number by the obtained average target base sequence number.

It is preferable to perform an operation of controlling the cell cycles before producing the cell suspension. By preparing the cells uniformly to a state before replication occurs or a state after replication has occurred, it is possible to calculate the number of target base sequences based on the cell number more accurately.

It is preferable to calculate a degree of certainty (probability) for the estimated specific copy number. By calculating a degree of certainty (probability), it is possible to express and output the degree of certainty as a variance or a standard deviation based on these values. When adding up influences of a plurality of factors, it is possible use a square root of the sum of the squares of the standard deviation commonly used. For example, a correct answer percentage for the number of cells discharged, the number of DNA in a cell, and a landing ratio at which discharged cells land in wells can be used as the factors. A highly influential factor may be selected for calculation.

<<<Liquid Droplet Landing Step>>>

The liquid droplet landing step is a step of discharging the cell suspension in the form of liquid droplets to sequentially land the liquid droplets in wells of a plate.

A liquid droplet means a gathering of a liquid formed by a surface tension.

Discharging means making the cell suspension fly in the form of liquid droplets.

"Sequentially" means "in order".

Landing means making liquid droplets reach the wells.

As a discharging unit, a unit configured to discharge the cell suspension in the form of liquid droplets (hereinafter may also be referred to as "discharging head") can be suitably used.

Examples of the method for discharging the cell suspension in the form of liquid droplets include an on-demand method and a continuous method that are based on the inkjet method. Of these methods, in the case of the continuous method, there is a tendency that the dead volume of the cell suspension used is high, because of, for example, empty discharging until the discharging state becomes stable, adjustment of the amount of liquid droplets, and continued formation of liquid droplets even during transfer between the wells. In the present disclosure, in terms of cell number adjustment, it is preferable to suppress influence due to the dead volume. Hence, of the two methods, the on-demand method is more preferable.

Examples of the on-demand method include a plurality of known methods such as a pressure applying method of applying a pressure to a liquid to discharge the liquid, a thermal method of discharging a liquid by film boiling due to heating, and an electrostatic method of drawing liquid droplets by electrostatic attraction to form liquid droplets. Among these methods, the pressure applying method is preferable for the reason described below.

In the electrostatic method, there is a need for disposing an electrode in a manner to face a discharging unit that is configured to retain the cell suspension and form liquid droplets. In the method for producing the device, a plate for receiving liquid droplets is disposed at the facing position. Hence, it is preferable not to provide an electrode, in order to increase the degree of latitude in the plate configuration.

In the thermal method, there are a risk of local heating concentration that may affect the cells, which are a biomaterial, and a risk of kogation to the heater portion. Influences by heat depend on the components contained or the purpose for which the plate is used. Therefore, there is no need for flatly rejecting the thermal method. However, the pressure applying method is preferable because the pressure applying method has a lower risk of kogation to the heater portion than the thermal method.

Examples of the pressure applying method include a method of applying a pressure to a liquid using a piezo element, and a method of applying a pressure using a valve such as an electromagnetic valve. The configuration example of a liquid droplet generating device usable for discharging liquid droplets of the cell suspension is illustrated in FIG. 10A to FIG. 10C.

Figure 10A:
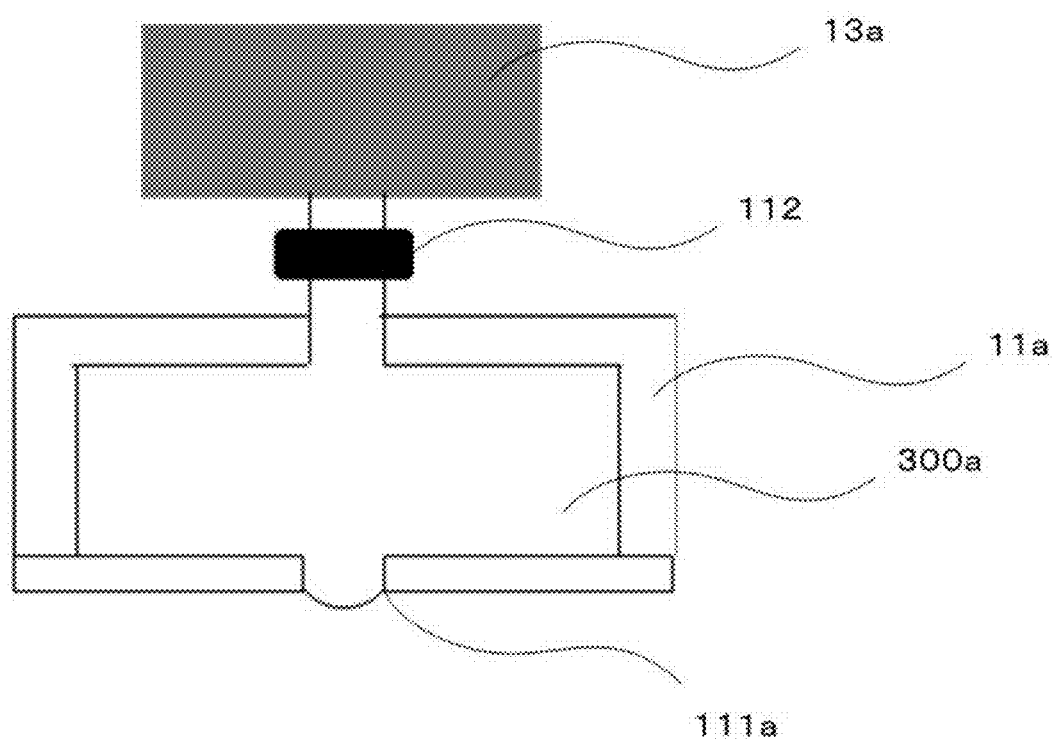
FIG. 10A is an exemplary diagram illustrating an example of an electromagnetic valve-type discharging head.

FIG. 10A is an exemplary diagram illustrating an example of an electromagnetic valve-type discharging head. The electromagnetic valve-type discharging head includes an electric motor 13a, an electromagnetic valve 112, a liquid chamber 11a, a cell suspension 300a, and a nozzle 111a.

As the electromagnetic valve-type discharging head, for example, a dispenser available from Tech Elan LLC can be suitably used.

Figure 10B:
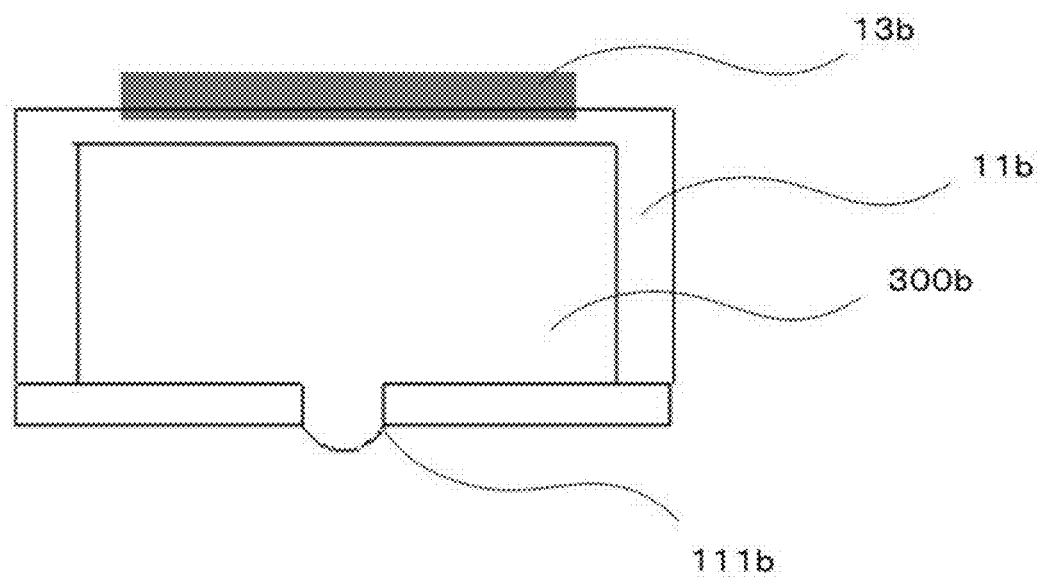
FIG. 10B is an exemplary diagram illustrating an example of a piezo-type discharging head.
Figure 10C:
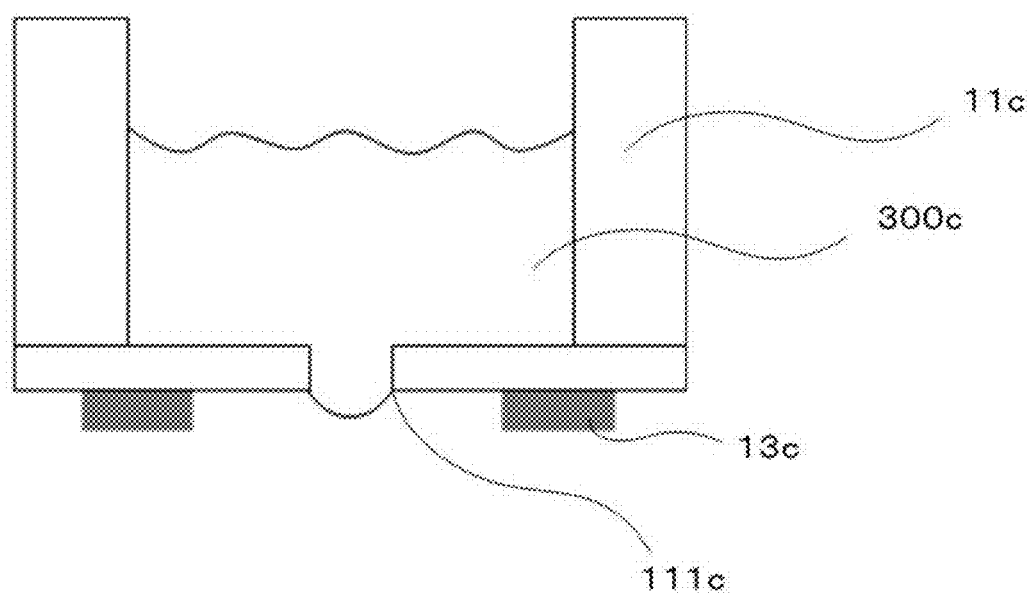
FIG. 10C is an exemplary diagram illustrating a modified example of the piezo-type discharging head illustrated in FIG. 10B.

FIG. 10B is an exemplary diagram illustrating an example of a piezo-type discharging head. The piezo-type discharging head includes a piezoelectric element 13b, a liquid chamber 11b, a cell suspension 300b, and a nozzle 111b.

As the piezo-type discharging head, for example, a single cell printer available from Cytena GmbH can be suitably used.

Any of these discharging heads may be used. However, the pressure applying method by the electromagnetic valve is not capable of forming liquid droplets at a high speed repeatedly. Therefore, it is preferable to use the piezo method in order to increase the throughput of producing a plate. A piezo-type discharging head using a common piezoelectric element 13b may cause unevenness in the cell concentration due to settlement, or may have nozzle clogging.

Therefore, a more preferable configuration is the configuration illustrated in FIG. 10C. FIG. 10C is an exemplary diagram of a modified example of a piezo-type discharging head using the piezoelectric element illustrated in FIG. 10B. The discharging head of FIG. 10C includes a piezoelectric element 13c, a liquid chamber 11c, a cell suspension 300c, and a nozzle 111c.

In the discharging head of FIG. 10C, when a voltage is applied to the piezoelectric element 13c from an unillustrated control device, a compressive stress is applied in the horizontal direction of the drawing sheet. This can deform the membrane in the upward-downward direction of the drawing sheet.

Examples of any other method than the on-demand method include a continuous method for continuously forming liquid droplets. When pushing out liquid droplets from a nozzle by pressurization, the continuous method applies regular fluctuations using a piezoelectric element or a heater, to make it possible to continuously form minute liquid droplets. Further, the continuous method can select whether to land a flying liquid droplet into a well or to recover the liquid droplet in a recovery unit, by controlling the discharging direction of the liquid droplet with voltage application. Such a method is employed in a cell sorter or a flow cytometer. For example, a device named: CELL SORTER SH800Z available from Sony Corporation can be used.

Figure 11A:
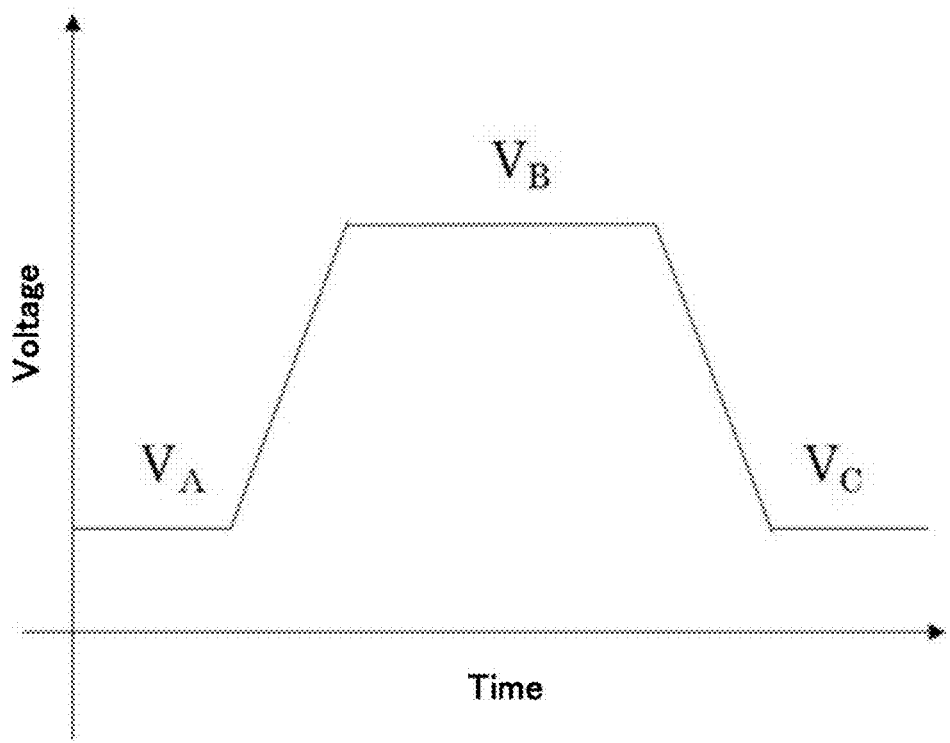
FIG. 11A is an exemplary graph plotting an example of a voltage applied to a piezoelectric element.
Figure 11B:
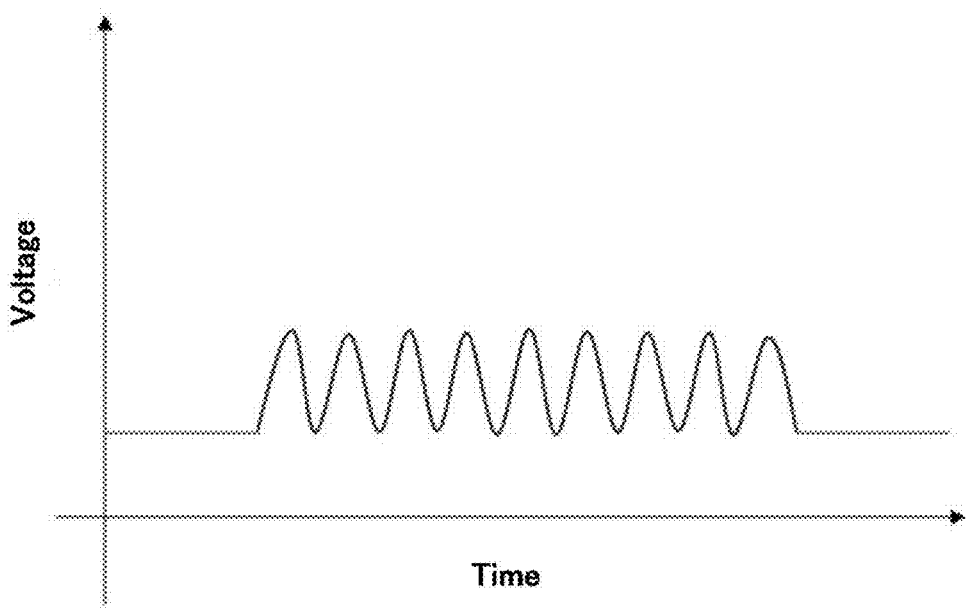
FIG. 11B is an exemplary graph plotting another example of a voltage applied to a piezoelectric element.

FIG. 11A is an exemplary graph plotting an example of a voltage applied to a piezoelectric element. FIG. 11B is an exemplary graph plotting another example of a voltage applied to a piezoelectric element. FIG. 11A plots a drive voltage for forming liquid droplets. Depending on the high or low level of the voltage ($V_A$, $V_B$, and $V_C$), it is possible to form liquid droplets. FIG. 11B plots a voltage for stirring the cell suspension without discharging liquid droplets.

During a period in which liquid droplets are not discharged, inputting a plurality of pulses that are not high enough to discharge liquid droplets enables the cell suspension in the liquid chamber to be stirred, making it possible to suppress occurrence of a concentration distribution due to settlement of the cells.

The liquid droplet forming operation of the discharging head that can be used in the present disclosure will be described below.

Figure 12A:
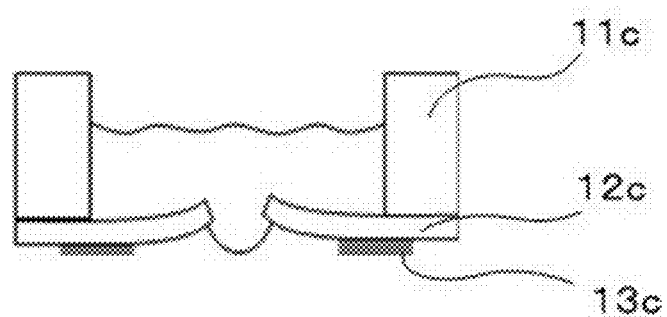
FIG. 12A is an exemplary diagram illustrating an example of a liquid droplet state.
Figure 12B:
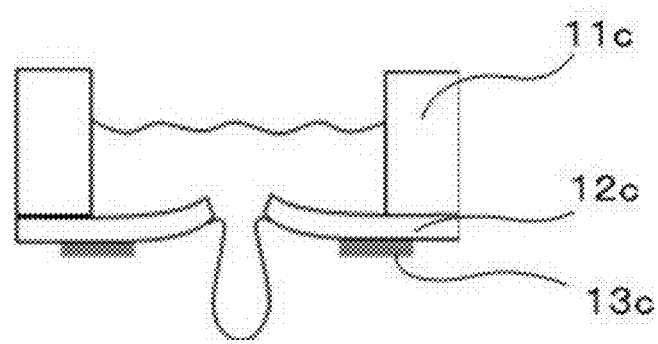
FIG. 12B is an exemplary diagram illustrating an example of a liquid droplet state.
Figure 12C:
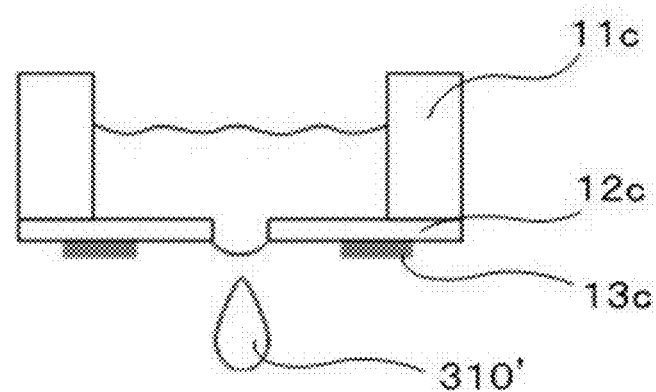
FIG. 12C is an exemplary diagram illustrating an example of a liquid droplet state.

The discharging head can discharge liquid droplets with application of a pulsed voltage to the upper and lower electrodes formed on the piezoelectric element. FIG. 12A to FIG. 12C are exemplary diagrams illustrating liquid droplet states at the respective timings.

In FIG. 12A, first, upon application of a voltage to the piezoelectric element 13c, a membrane 12c abruptly deforms to cause a high pressure between the cell suspension retained in the liquid chamber 11c and the membrane 12c. This pressure pushes out a liquid droplet outward through the nozzle portion.

Next, as illustrated in FIG. 12B, for a period of time until when the pressure relaxes upward, the liquid is continuously pushed out through the nozzle portion, to grow the liquid droplet.

Finally, as illustrated in FIG. 12C, when the membrane 12c returns to the original state, the liquid pressure about the interface between the cell suspension and the membrane 12c lowers, to form a liquid droplet 310'.

In the method for producing a device, a plate in which wells are formed is secured on a movable stage, and by combination of driving of the stage with formation of liquid droplets from the discharging head, liquid droplets are sequentially landed in the concaves. A method of moving the plate along with moving the stage is described here. However, naturally, it is also possible to move the discharging head.

The plate is not particularly limited, and a plate that is commonly used in bio fields and in which wells are formed can be used.

The number of wells in the plate is not particularly limited and may be appropriately selected depending on the intended purpose. The number of wells may be a single number or a plural number.

Figure 13:
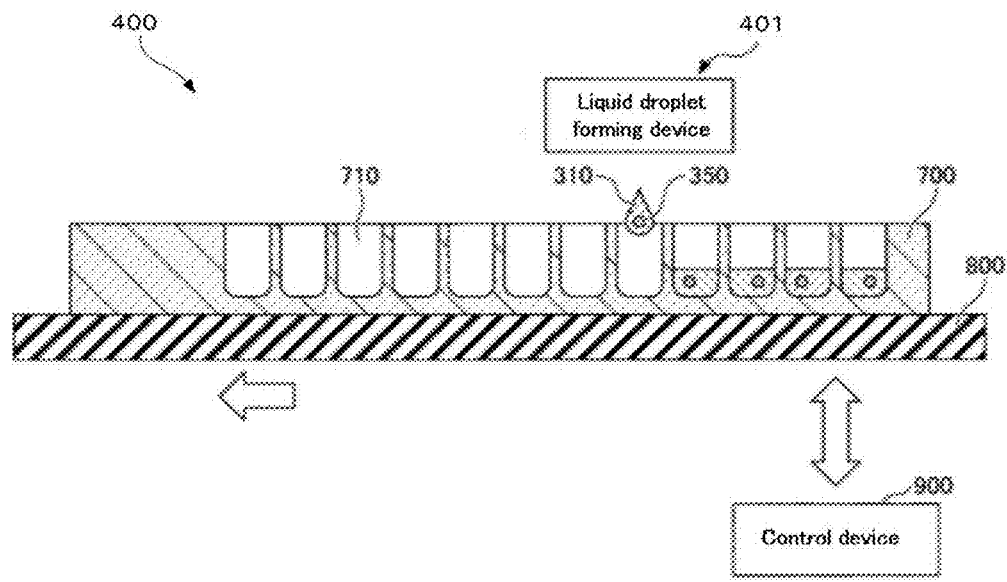
FIG. 13 is a schematic diagram illustrating an example of a dispensing device configured to land liquid droplets sequentially into wells.

FIG. 13 is a schematic diagram illustrating an example of a dispensing device 400 configured to land liquid droplets sequentially into wells of a plate.

As illustrated in FIG. 13, the dispensing device 400 configured to land liquid droplets includes a liquid droplet forming device 401, a plate 700, a stage 800, and a control device 900.

In the dispensing device 400, the plate 700 is disposed over a movable stage 800. The plate 700 has a plurality of wells 710 (concaves) in which liquid droplets 310 discharged from a discharging head of the liquid droplet forming device 401 land. The control device 900 is configured to move the stage 800 and control the relative positional relationship between the discharging head of the liquid droplet forming device 401 and each well 710. This enables liquid droplets 310 containing fluorescent-stained cells 350 to be discharged sequentially into the wells 710 from the discharging head of the liquid droplet forming device 401.

The control device 900 may be configured to include, for example, a CPU, a ROM, a RAM, and a main memory. In this case, various functions of the control device 900 can be realized by a program recorded in, for example, the ROM being read out into the main memory and executed by the CPU. However, a part or the whole of the control device 900 may be realized only by hardware. Alternatively, the control device 900 may be configured with, for example, physically a plurality of devices.

When landing the cell suspension into the wells, it is preferable to land the liquid droplets to be discharged into the wells, in a manner that a plurality of levels are obtained.

A plurality of levels mean a plurality of references serving as standards.

As the plurality of levels, it is preferable that a plurality of cells including a specific nucleic acid have a predetermined concentration gradient in the wells. With a concentration gradient, the nucleic acid can be favorably used as a reagent for calibration curve. The plurality of levels can be controlled using values counted by a sensor.

As the plate, it is preferable to use, for example, a 1-well microtube, 8-series tubes, a 96-well plate, and a 384-well plate. When the number of wells are a plural number, it is possible to dispense the same number of cells into the wells of these plates, or it is also possible to dispense numbers of cells of different levels into the wells. There may be a well in which no cells are contained. Particularly, for producing a plate used for evaluating a real-time PCR device or digital PCR device configured to quantitatively evaluate an amount of nucleic acids, it is preferable to dispense numbers of nucleic acids of a plurality of levels. For example, it is conceivable to produce a plate into which cells (or nucleic acids) are dispensed at 7 levels, namely about 1 cell, 2 cells, 4 cells, 8 cells, 16 cells, 32 cells, and 64 cells. Using such a plate, it is possible to inspect, for example, quantitativity, linearity, and lower limit of evaluation of a real-time PCR device or digital PCR device.

<<<Cell Number Counting Step>>>

The cell number counting step is a step of counting the number of cells contained in the liquid droplets with a sensor after the liquid droplets are discharged and before the liquid droplets land in the wells.

A sensor means a device configured to, by utilizing some scientific principles, change mechanical, electromagnetic, thermal, acoustic, or chemical properties of natural phenomena or artificial products or spatial information/temporal information indicated by these properties into signals, which are a different medium easily handleable by humans or machines.

Counting means counting of numbers.

The cell number counting step is not particularly limited and may be appropriately selected depending on the intended purpose, so long as the cell number counting step counts the number of cells contained in the liquid droplets with a sensor after the liquid droplets are discharged and before the liquid droplets land in the wells. The cell number counting step may include an operation for observing cells before discharging and an operation for counting cells after landing.

For counting the number of cells contained in the liquid droplets after the liquid droplets are discharged and before the liquid droplets land in the wells, it is preferable to observe cells in a liquid droplet at a timing at which the liquid droplet is at a position that is immediately above a well opening and at which the liquid droplet is predicted to enter the well in the plate without fail.

Examples of the method for observing cells in a liquid droplet include an optical detection method and an electric or magnetic detection method.

—Optical Detection Method—

Figure 14:
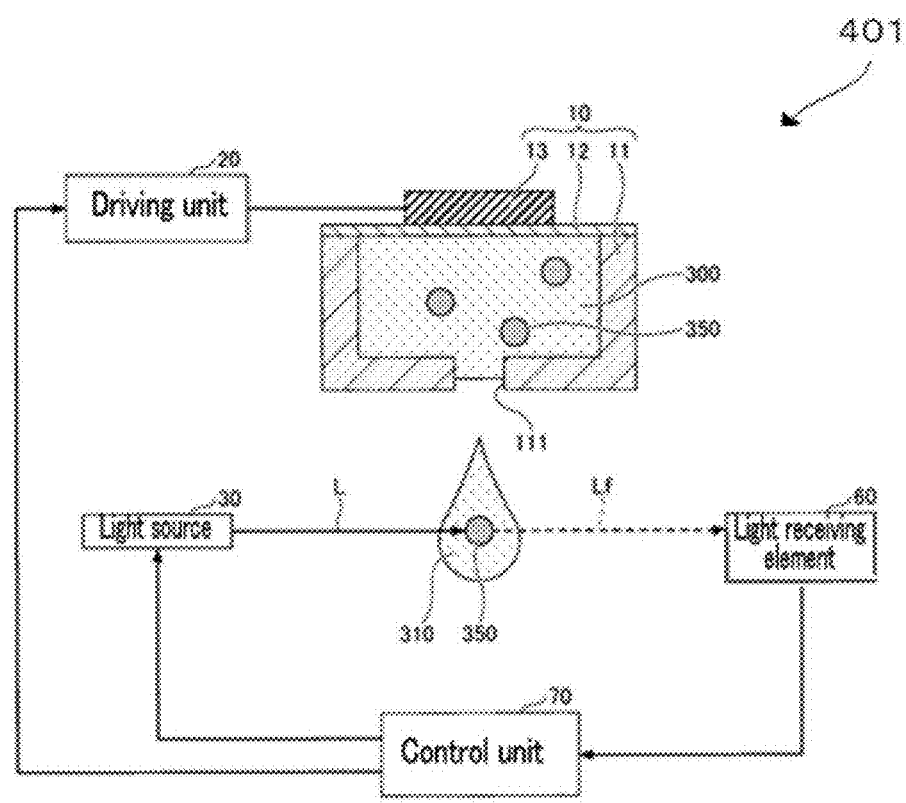
FIG. 14 is an exemplary diagram illustrating an example of a liquid droplet forming device.
Figure 18:
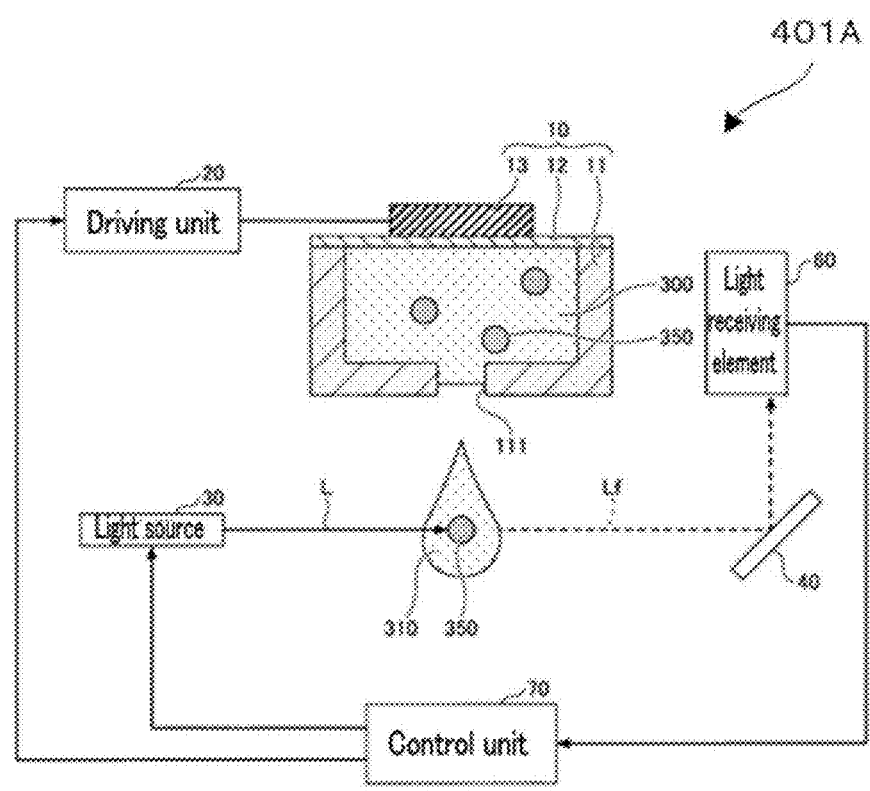
FIG. 18 is an exemplary diagram illustrating a modified example of a liquid droplet forming device.
Figure 19:
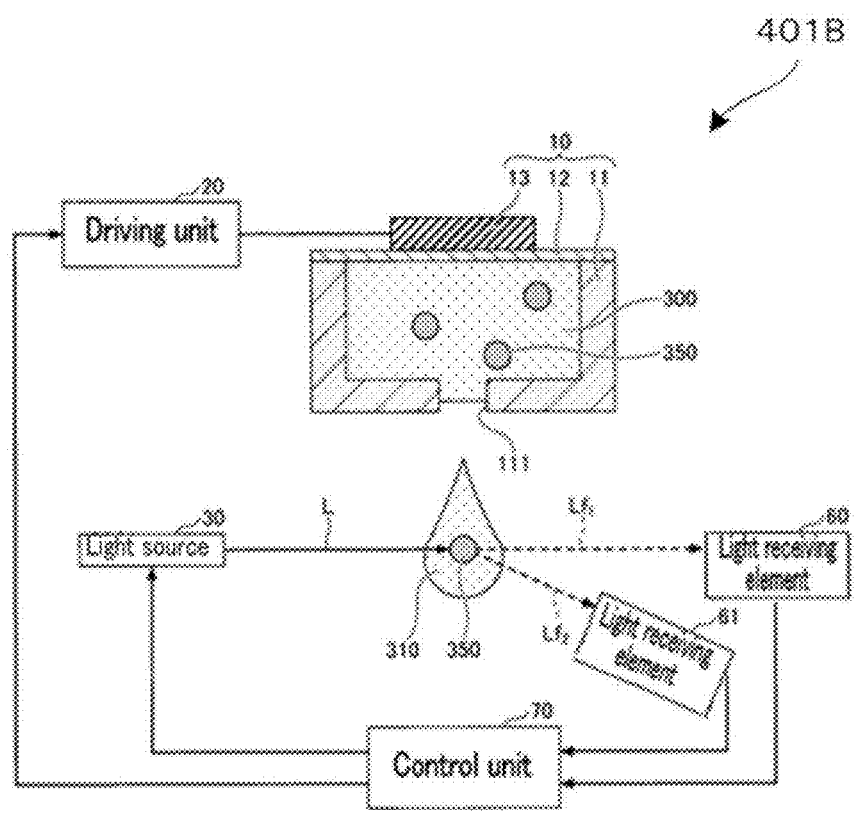
FIG. 19 is an exemplary diagram illustrating another modified example of a liquid droplet forming device.

With reference to FIG. 14, FIG. 18, and FIG. 19, an optical detection method will be described below.

FIG. 14 is an exemplary diagram illustrating an example of a liquid droplet forming device 401. FIG. 18 and FIG. 19 are exemplary diagrams illustrating other examples of liquid droplet forming devices 401A and 401B. As illustrated in FIG. 14, the liquid droplet forming device 401 includes a discharging head (liquid droplet discharging unit) 10, a driving unit 20, a light source 30, a light receiving element 60, and a control unit 70.

In FIG. 14, a liquid obtained by dispersing cells in a predetermined solution after fluorescently staining the cells with a specific pigment is used as the cell suspension. Cells are counted by irradiating the liquid droplets formed by the discharging head with light having a specific wavelength and emitted from the light source and detecting fluorescence emitted by the cells with the light receiving element. Here, autofluorescence emitted by molecules originally contained in the cells may be utilized, in addition to the method of staining the cells with a fluorescent pigment. Alternatively, genes for producing fluorescent proteins (for example, GFP (Green Fluorescent Proteins)) may be previously introduced into the cells, in order that the cells may emit fluorescence.

Irradiation of light means application of light.

The discharging head 10 includes a liquid chamber 11, a membrane 12, and a driving element 13 and can discharge a cell suspension 300 suspending fluorescent-stained cells 350 in the form of liquid droplets.

The liquid chamber 11 is a liquid retaining portion configured to retain the cell suspension 300 suspending the fluorescent-stained cells 350. A nozzle 111, which is a through hole, is formed in the lower surface of the liquid chamber 11. The liquid chamber 11 may be formed of, for example, a metal, silicon, or a ceramic. Examples of the fluorescent-stained cells 350 include inorganic particles and organic polymer particles stained with a fluorescent pigment.

The membrane 12 is a film-shaped member secured on the upper end portion of the liquid chamber 11. The planar shape of the membrane 12 may be, for example, a circular shape, but may also be, for example, an elliptic shape or a quadrangular shape.

The driving element 13 is provided on the upper surface of the membrane 12. The shape of the driving element 13 may be designed to match the shape of the membrane 12. For example, when the planar shape of the membrane 12 is a circular shape, it is preferable to provide a circular driving element 13.

The membrane 12 can be vibrated by supplying a driving signal to the driving element 13 from a driving unit 20. The vibration of the membrane 12 can cause a liquid droplet 310 containing the fluorescent-stained cells 350 to be discharged through the nozzle 111.

When a piezoelectric element is used as the driving element 13, for example, the driving element 13 may have a structure obtained by providing the upper surface and the lower surface of the piezoelectric material with electrodes across which a voltage is to be applied. In this case, when the driving unit 20 applies a voltage across the upper and lower electrodes of the piezoelectric element, a compressive stress is applied in the horizontal direction of the drawing sheet, making it possible for the membrane 12 to vibrate in the upward-downward direction of the drawing sheet. As the piezoelectric material, for example, lead zirconate titanate (PZT) may be used. In addition, various piezoelectric materials can be used, such as bismuth iron oxide, metal niobate, barium titanate, or materials obtained by adding metals or different oxides to these materials.

The light source 30 is configured to irradiate a flying liquid droplet 310 with light L. A flying state means a state from when the liquid droplet 310 is discharged from a liquid droplet discharging unit 10 until when the liquid droplet 310 lands on the landing target. A flying liquid droplet 310 has an approximately spherical shape at the position at which the liquid droplet 310 is irradiated with the light L. The beam shape of the light L is an approximately circular shape.

It is preferable that the beam diameter of the light L be from about 10 times through 100 times as great as the diameter of the liquid droplet 310. This is for ensuring that the liquid droplet 310 is irradiated with the light L from the light source 30 without fail even when the position of the liquid droplet 310 fluctuates.

However, it is not preferable if the beam diameter of the light L is much greater than 100 times as great as the diameter of the liquid droplet 310. This is because the energy density of the light with which the liquid droplet 310 is irradiated is reduced, to lower the light volume of fluorescence Lf to be emitted upon the light L serving as excitation light, making it difficult for the light receiving element 60 to detect the fluorescence Lf.

It is preferable that the light L emitted by the light source 30 be pulse light. It is preferable to use, for example, a solid-state laser, a semiconductor laser, and a dye laser. When the light L is pulse light, the pulse width is preferably 10 microseconds or less and more preferably 1 microsecond or less. The energy per unit pulse is preferably roughly 0.1 microjoules or higher and more preferably 1 microjoule or higher, although significantly depending on the optical system such as presence or absence of light condensation.

The light receiving element 60 is configured to receive fluorescence Lf emitted by the fluorescent-stained cell 350 upon absorption of the light L as excitation light, when the fluorescent-stained cell 350 is contained in a flying liquid droplet 310. Because the fluorescence Lf is emitted to all directions from the fluorescent-stained cell 350, the light receiving element 60 can be disposed at an arbitrary position at which the fluorescence Lf is receivable. Here, in order to improve contrast, it is preferable to dispose the light receiving element 60 at a position at which direct incidence of the light L emitted by the light source 30 to the light receiving element 60 does not occur.

The light receiving element 60 is not particularly limited and may be appropriately selected depending on the intended purpose so long as the light receiving element 60 is an element capable of receiving the fluorescence Lf emitted by the fluorescent-stained cell 350. An optical sensor configured to receive fluorescence from a cell in a liquid droplet when the liquid droplet is irradiated with light having a specific wavelength is preferable. Examples of the light receiving element 60 include one-dimensional elements such as a photodiode and a photosensor. When high-sensitivity measurement is needed, it is preferable to use a photomultiplier tube and an Avalanche photodiode. As the light receiving element 60, two-dimensional elements such as a CCD (Charge Coupled Device), a CMOS (Complementary Metal Oxide Semiconductor), and a gate CCD may be used.

The fluorescence Lf emitted by the fluorescent-stained cell 350 is weaker than the light L emitted by the light source 30. Therefore, a filter configured to attenuate the wavelength range of the light L may be installed at a preceding stage (light receiving surface side) of the light receiving element 60. This enables the light receiving element 60 to obtain an extremely highly contrastive image of the fluorescent-stained cell 350. As the filter, for example, a notch filter configured to attenuate a specific wavelength range including the wavelength of the light L may be used.

As described above, it is preferable that the light L emitted by the light source 30 be pulse light. The light L emitted by the light source 30 may be continuously oscillating light. In this case, it is preferable to control the light receiving element 60 to be capable of receiving light at a timing at which a flying liquid droplet 310 is irradiated with the continuously oscillating light, to make the light receiving element 60 receive the fluorescence Lf.

Figure 15:
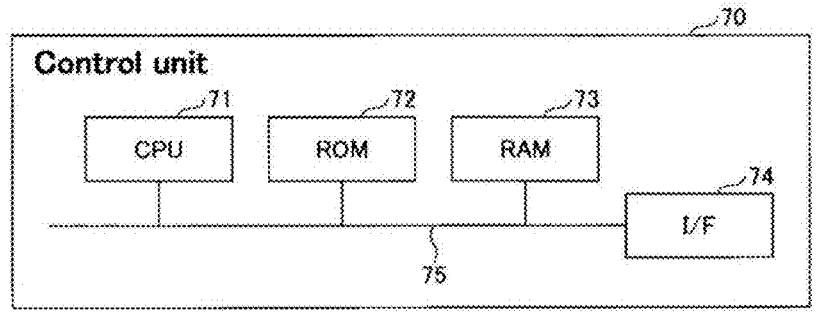
FIG. 15 is a diagram illustrating hardware blocks of a control unit of the liquid droplet forming device of FIG. 14.
Figure 16:
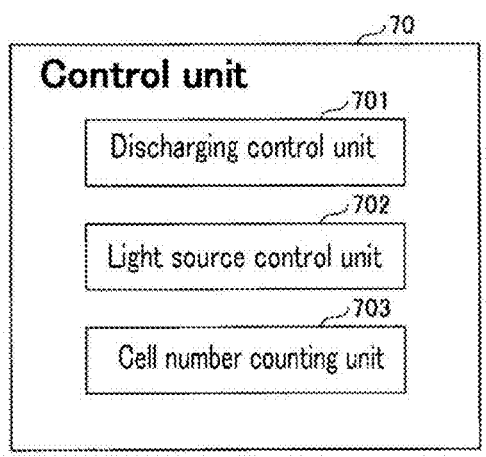
FIG. 16 is a diagram illustrating functional blocks of a control unit of the liquid droplet forming device of FIG. 15.
Figure 17:
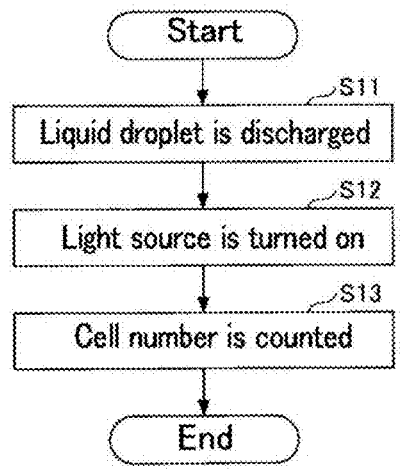
FIG. 17 is a flowchart illustrating an example of an operation of a liquid droplet forming device.

The control unit 70 has a function of controlling the driving unit 20 and the light source 30. The control unit 70 also has a function of obtaining information that is based on the light volume received by the light receiving element 60 and counting the number of fluorescent-stained cells 350 contained in the liquid droplet 310 (the case where the number is zero is also included). With reference to FIG. 15 to FIG. 17, an operation of the liquid droplet forming device 401 including an operation of the control unit 70 will be described below.

FIG. 15 is a diagram illustrating hardware blocks of the control unit of the liquid droplet forming device of FIG. 14. FIG. 16 is a diagram illustrating functional blocks of the control unit of the liquid droplet forming device of FIG. 14. FIG. 17 is a flowchart illustrating an example of the operation of the liquid droplet forming device.

As illustrated in FIG. 15, the control unit 70 includes a CPU 71, a ROM 72, a RAM 73, an I/F 74, and a bus line 75. The CPU 71, the ROM 72, the RAM 73, and the I/F 74 are coupled to one another via the bus line 75.

The CPU 71 is configured to control various functions of the control unit 70. The ROM 72 serving as a memory unit is configured to store programs to be executed by the CPU 71 for controlling the various functions of the control unit 70 and various information. The RAM 73 serving as a memory unit is configured to be used as, for example, the work area of the CPU 71. The RAM 73 is also configured to be capable of storing predetermined information for a temporary period of time. The I/F 74 is an interface configured to couple the liquid droplet forming device 401 to, for example, another device. The liquid droplet forming device 401 may be coupled to, for example, an external network via the I/F 74.

As illustrated in FIG. 16, the control unit 70 includes a discharging control unit 701, a light source control unit 702, and a cell number counting unit (cell number sensing unit) 703 as functional blocks.

With reference to FIG. 16 and FIG. 17, cell number counting by the liquid droplet forming device 401 will be described.

In the step S11, the discharging control unit 701 of the control unit 70 outputs an instruction for discharging to the driving unit 20. Upon reception of the instruction for discharging from the discharging control unit 701, the driving unit 20 supplies a driving signal to the driving element 13 to vibrate the membrane 12. The vibration of the membrane 12 causes a liquid droplet 310 containing a fluorescent-stained cell 350 to be discharged through the nozzle 111.

Next, in the step S12, the light source control unit 702 of the control unit 70 outputs an instruction for lighting to the light source 30 in synchronization with the discharging of the liquid droplet 310 (in synchronization with a driving signal supplied by the driving unit 20 to the liquid droplet discharging unit 10). In accordance with this instruction, the light source 30 is turned on to irradiate the flying liquid droplet 310 with the light L.

Here, the light is emitted by the light source 30, not in synchronization with discharging of the liquid droplet 310 by the liquid droplet discharging unit 10 (supplying of the driving signal to the liquid droplet discharging unit 10 by the driving unit 20), but in synchronization with the timing at which the liquid droplet 310 has come flying to a predetermined position in order for the liquid droplet 310 to be irradiated with the light L. That is, the light source control unit 702 controls the light source 30 to emit light at a predetermined period of time of delay from the discharging of the liquid droplet 310 by the liquid droplet discharging unit 10 (from the driving signal supplied by the driving unit 20 to the liquid droplet discharging unit 10).

For example, the speed v of the liquid droplet 310 to be discharged when the driving signal is supplied to the liquid droplet discharging unit 10 may be measured beforehand. Based on the measured speed v, the time t taken from when the liquid droplet 310 is discharged until when the liquid droplet 310 reaches the predetermined position may be calculated, in order that the timing of light irradiation by the light source 30 may be delayed from the timing at which the driving signal is supplied to the liquid droplet discharging unit 10 by the period of time oft. This enables a good control on light emission, and can ensure that the liquid droplet 310 is irradiated with the light from the light source 30 without fail.

Next, in the step S13, the cell number counting unit 703 of the control unit 70 counts the number of fluorescent-stained cells 350 contained in the liquid droplet 310 (the case where the number is zero is also included) based on information from the light receiving element 60. The information from the light receiving element 60 indicates the luminance (light volume) and the area value of the fluorescent-stained cell 350.

The cell number counting unit 703 can count the number of fluorescent-stained cells 350 by, for example, comparing the light volume received by the light receiving element 60 with a predetermined threshold. In this case, a one-dimensional element may be used or a two-dimensional element may be used as the light receiving element 60.

When a two-dimensional element is used as the light receiving element 60, the cell number counting unit 703 may use a method of performing image processing for calculating the luminance or the area of the fluorescent-stained cell 350 based on a two-dimensional image obtained from the light receiving element 60. In this case, the cell number counting unit 703 can count the number of fluorescent-stained cells 350 by calculating the luminance or the area value of the fluorescent-stained cell 350 by image processing and comparing the calculated luminance or area value with a predetermined threshold.

The fluorescent-stained cell 350 may be a cell or a stained cell. A stained cell means a cell stained with a fluorescent pigment or a cell that can express a fluorescent protein.

The fluorescent pigment for the stained cell is not particularly limited and may be appropriately selected depending on the intended purpose. Examples of the fluorescent pigment include fluoresceins, rhodamines, coumarins, pyrenes, cyanines, and azo pigments. One of these fluorescent pigments may be used alone or two or more of these fluorescent pigments may be used in combination. Among these fluorescent pigments, eosin, Evans blue, trypan blue, rhodamine 6G, rhodamine B, and Rhodamine 123 are more preferable.

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. One of these fluorescent proteins may be used alone or two or more of these fluorescent proteins may be used in combination.

In this way, in the liquid droplet forming device 401, the driving unit 20 supplies a driving signal to the liquid droplet discharging unit 10 retaining the cell suspension 300 suspending fluorescent-stained cells 350 to cause the liquid droplet discharging unit 10 to discharge a liquid droplet 310 containing the fluorescent-stained cell 350, and the flying liquid droplet 310 is irradiated with the light L from the light source 30. Then, the fluorescent-stained cell 350 contained in the flying liquid droplet 310 emits the fluorescence Lf upon the light L serving as excitation light, and the light receiving element 60 receives the fluorescence Lf. Then, the cell number counting unit 703 counts the number of fluorescent-stained cells 350 contained in the flying liquid droplet 310, based on information from the light receiving element 60.

That is, the liquid droplet forming device 401 is configured for on-the-spot actual observation of the number of fluorescent-stained cells 350 contained in the flying liquid droplet 310. This can realize a better accuracy than hitherto obtained, in counting the number of fluorescent-stained cells 350. Moreover, because the fluorescent-stained cell 350 contained in the flying liquid droplet 310 is irradiated with the light L and emits the fluorescence Lf that is to be received by the light receiving element 60, an image of the fluorescent-stained cell 350 can be obtained with a high contrast, and the frequency of occurrence of erroneous counting of the number of fluorescent-stained cells 350 can be reduced.

FIG. 18 is an exemplary diagram illustrating a modified example of the liquid droplet forming device 401 of FIG. 14. As illustrated in FIG. 18, a liquid droplet forming device 401A is different from the liquid droplet forming device 401 (see FIG. 14) in that a mirror 40 is arranged at the preceding stage of the light receiving element 60. Description about components that are the same as in the embodiment already described may be skipped.

In the liquid droplet forming device 401A, arranging the mirror 40 at the perceiving stage of the light receiving element 60 can improve the degree of latitude in the layout of the light receiving element 60.

For example, in the layout of FIG. 14, when a nozzle 111 and a landing target are brought close to each other, there is a risk of occurrence of interference between the landing target and the optical system (particularly, the light receiving element 60) of the liquid droplet forming device 401. With the layout of FIG. 18, occurrence of interference can be avoided.

That is, by changing the layout of the light receiving element 60 as illustrated in FIG. 18, it is possible to reduce the distance (gap) between the landing target on which a liquid droplet 310 is landed and the nozzle 111 and suppress landing on a wrong position. As a result, the dispensing accuracy can be improved.

FIG. 19 is an exemplary diagram illustrating another modified example of the liquid droplet forming device 401 of FIG. 14. As illustrated in FIG. 19, a liquid droplet forming device 401B is different from the liquid droplet forming device 401 (see FIG. 14) in that a light receiving element 61 configured to receive fluorescence $Lf_2$ emitted by the fluorescent-stained cell 350 is provided in addition to the light receiving element 60 configured to receive fluorescence $Lf_1$ emitted by the fluorescent-stained cell 350. Description about components that are the same as in the embodiment already described may be skipped.

The fluorescences $Lf_1$ and $Lf_2$ represent parts of fluorescence emitted to all directions from the fluorescent-stained cell 350. The light receiving elements 60 and 61 can be disposed at arbitrary positions at which the fluorescence emitted to different directions by the fluorescent-stained cell 350 is receivable. Three or more light receiving elements may be disposed at positions at which the fluorescence emitted to different directions by the fluorescent-stained cell 350 is receivable. The light receiving elements may have the same specifications or different specifications.

With one light receiving element, when a plurality of fluorescent-stained cells 350 are contained in a flying liquid droplet 310, there is a risk that the cell number counting unit 703 may erroneously count the number of fluorescent-stained cells 350 contained in the liquid droplet 310 (a risk that a counting error may occur) because the fluorescent-stained cells 350 may overlap each other.

Figure 20A:
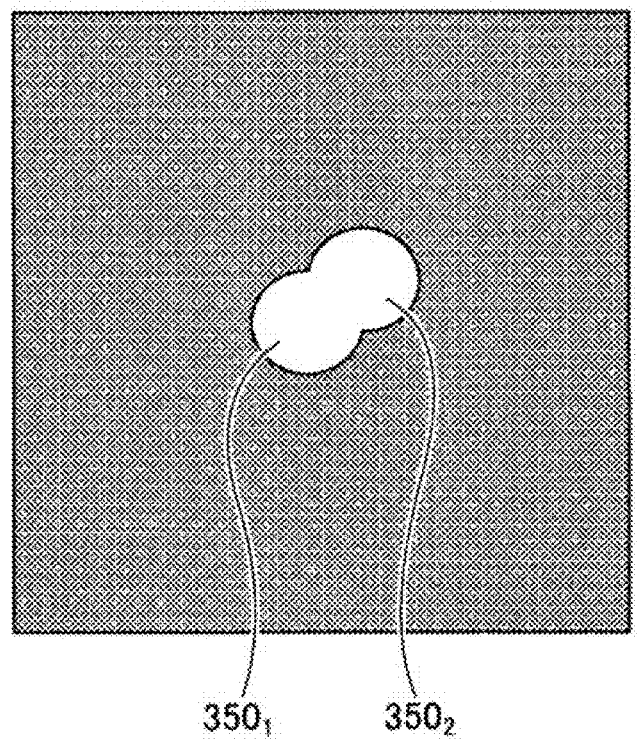
FIG. 20A is a diagram illustrating a case where two fluorescent particles are contained in a flying liquid droplet.
Figure 20B:
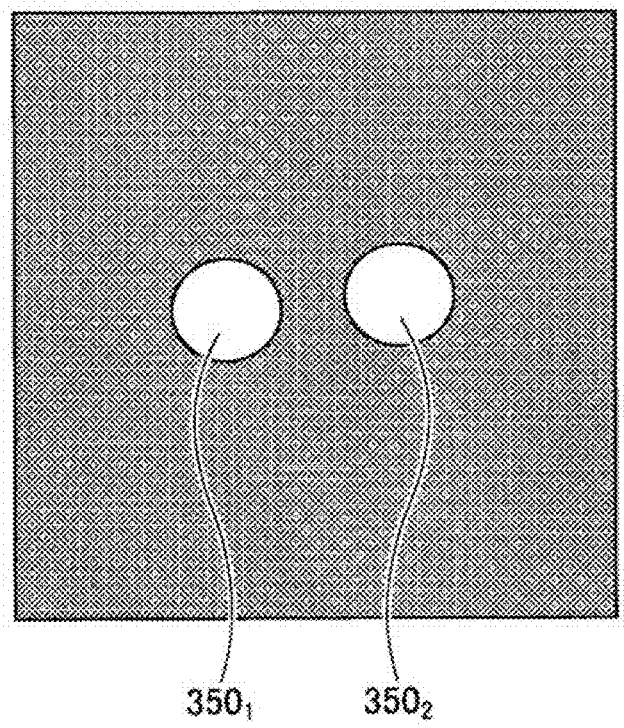
FIG. 20B is a diagram illustrating a case where two fluorescent particles are contained in a flying liquid droplet.

FIG. 20A and FIG. 20B are diagrams illustrating a case where two fluorescent-stained cells are contained in a flying liquid droplet. For example, as illustrated in FIG. 20A, there may be a case where fluorescent-stained cells 3501 and 3502 overlap each other, or as illustrated in FIG. 20B, there may be a case where the fluorescent-stained cells 3501 and 3502 do not overlap each other. By providing two or more light receiving elements, it is possible to reduce the influence of overlap of the fluorescent-stained cells.

As described above, the cell number counting unit 703 can count the number of fluorescent particles, by calculating the luminance or the area value of fluorescent particles by image processing and comparing the calculated luminance or area value with a predetermined threshold.

When two or more light receiving elements are installed, it is possible to suppress occurrence of a counting error, by adopting the data indicating the maximum value among the luminance values or area values obtained from these light receiving elements. This will be described in more detail with reference to FIG. 21.

Figure 21:
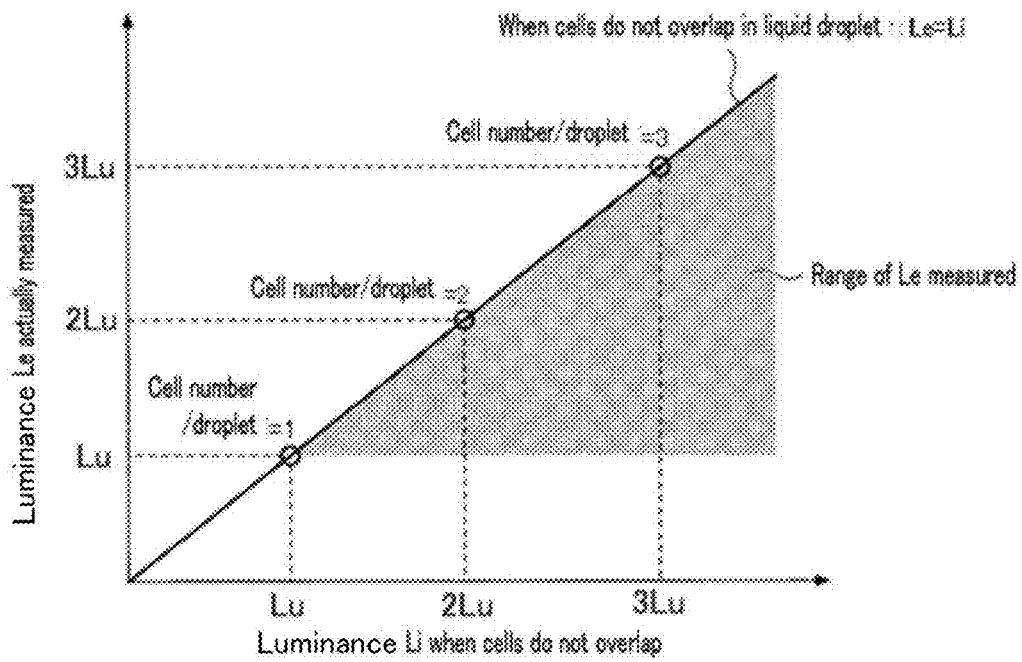
FIG. 21 is a graph plotting an example of a relationship between a luminance Li when particles do not overlap each other and a luminance Le actually measured.

FIG. 21 is a graph plotting an example of a relationship between a luminance Li when particles do not overlap each other and a luminance Le actually measured. As plotted in FIG. 21, when particles in the liquid droplet do not overlap each other, Le is equal to Li. For example, in the case where the luminance of one cell is assumed to be Lu, Le is equal to Lu when the number of cells per droplet is 1, and Le is equal to nLu when the number of particles per droplet is n (n: natural number).

However, actually, when n is 2 or greater, because particles may overlap each other, the luminance to be actually measured is Lu≤Le≤nLu (the half-tone dot meshed portion in FIG. 21). Hence, when the number of cells per droplet is n, the threshold may be set to, for example, (nLu−Lu/2) ≤threshold<(nLu+Lu/2). When a plurality of light receiving elements are installed, it is possible to suppress occurrence of a counting error, by adopting the maximum value among the data obtained from these light receiving elements. An area value may be used instead of luminance.

When a plurality of light receiving elements are installed, the number of cells may be determined according to an algorithm for estimating the number of cells based on a plurality of shape data to be obtained.

As can be understood, with the plurality of light receiving elements configured to receive fluorescence emitted to different directions by the fluorescent-stained cell 350, the liquid droplet forming device 401B can further reduce the frequency of occurrence of erroneous counting of the number of fluorescent-stained cells 350.

Figure 22:
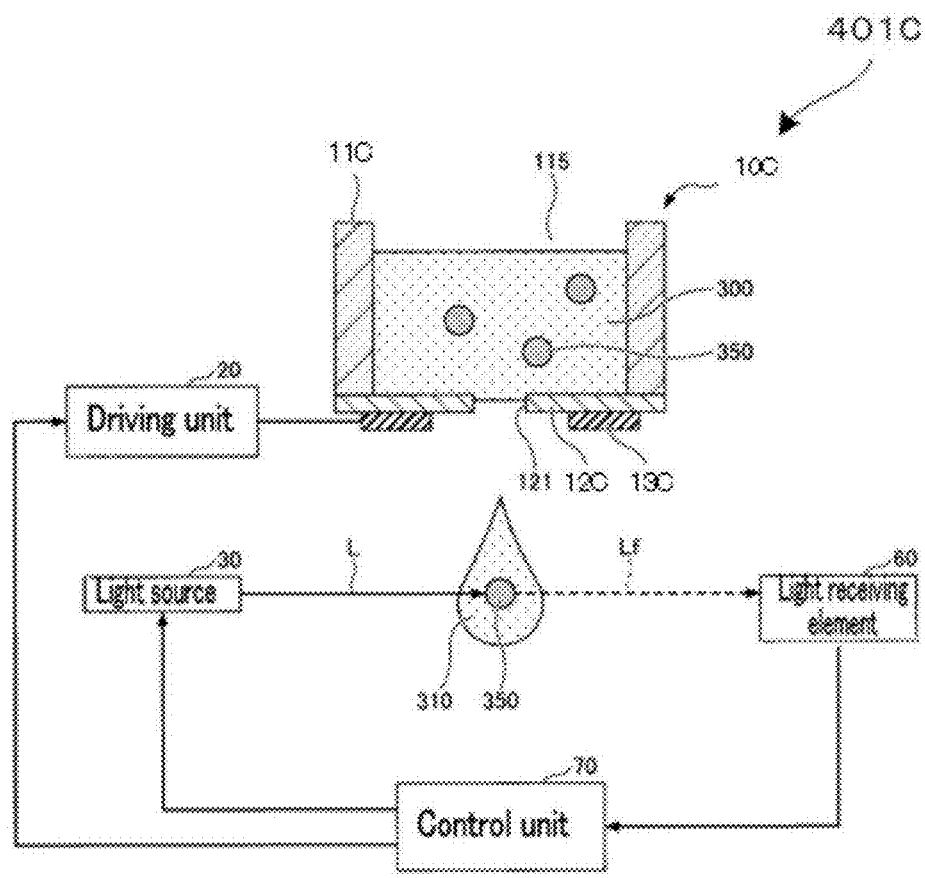
FIG. 22 is an exemplary diagram illustrating another modified example of a liquid droplet forming device.

FIG. 22 is an exemplary diagram illustrating another modified example of the liquid droplet forming device 401 of FIG. 14. As illustrated in FIG. 22, a liquid droplet forming device 401C is different from the liquid droplet forming device 401 (see FIG. 14) in that a liquid droplet discharging unit 10C is provided instead of the liquid droplet discharging unit 10. Description about components that are the same as in the embodiment already described may be skipped.

The liquid droplet discharging unit 10C includes a liquid chamber 11C, a membrane 12C, and a driving element 13C. At the top, the liquid chamber 11C has an atmospherically exposed portion 115 configured to expose the interior of the liquid chamber 11C to the atmosphere, and bubbles mixed in the cell suspension 300 can be evacuated through the atmospherically exposed portion 115.

The membrane 12C is a film-shaped member secured at the lower end of the liquid chamber 11C. A nozzle 121, which is a through hole, is formed in approximately the center of the membrane 12C, and the vibration of the membrane 12C causes the cell suspension 300 retained in the liquid chamber 11C to be discharged through the nozzle 121 in the form of a liquid droplet 310. Because the liquid droplet 310 is formed by the inertia of the vibration of the membrane 12C, it is possible to discharge the cell suspension 300 even when the cell suspension 300 has a high surface tension (a high viscosity). The planer shape of the membrane 12C may be, for example, a circular shape, but may also be, for example, an elliptic shape or a quadrangular shape.

The material of the membrane 12C is not particularly limited. However, if the material of the membrane 12C is extremely flexible, the membrane 12C easily undergo vibration and is not easily able to stop vibration immediately when there is no need for discharging. Therefore, a material having a certain degree of hardness is preferable. As the material of the membrane 12C, for example, a metal material, a ceramic material, and a polymeric material having a certain degree of hardness can be used.

Particularly, when a cell is used as the fluorescent-stained cell 350, the material of the membrane is preferably a material having a low adhesiveness with the cell or proteins. Generally, adhesiveness of cells is said to be dependent on the contact angle of the material with respect to water. When the material has a high hydrophilicity or a high hydrophobicity, the material has a low adhesiveness with cells. As the material having a high hydrophilicity, various metal materials and ceramics (metal oxides) can be used. As the material having a high hydrophobicity, for example, fluororesins can be used.

Other examples of such materials include stainless steel, nickel, and aluminum, and silicon dioxide, alumina, and zirconia. In addition, it is conceivable to reduce cell adhesiveness by coating the surface of the material. For example, it is possible to coat the surface of the material with the metal or metal oxide materials described above, or coat the surface of the material with a synthetic phospholipid polymer mimicking a cellular membrane (e.g., LIPIDURE available from NOF Corporation).

It is preferable that the nozzle 121 be formed as a through hole having a substantially perfect circle shape in approximately the center of the membrane 12C. In this case, the diameter of the nozzle 121 is not particularly limited but is preferably twice or more greater than the size of the fluorescent-stained cell 350 in order to prevent the nozzle 121 from being clogged with the fluorescent-stained cell 350. When the fluorescent-stained cell 350 is, for example, an animal cell, particularly, a human cell, the diameter of the nozzle 121 is preferably 10 micrometers or greater and more preferably 100 micrometers or greater in conformity with the cell used, because a human cell typically has a size of about from 5 micrometers through 50 micrometers.

On the other hand, when a liquid droplet is extremely large, it is difficult to achieve an object of forming a minute liquid droplet. Therefore, the diameter of the nozzle 121 is preferably 200 micrometers or less. That is, in the liquid droplet discharging unit 10C, the diameter of the nozzle 121 is typically in the range of from 10 micrometers through 200 micrometers.

The driving element 13C is formed on the lower surface of the membrane 12C. The shape of the driving element 13C can be designed to match the shape of the membrane 12C. For example, when the planar shape of the membrane 12C is a circular shape, it is preferable to form a driving element 13C having an annular (ring-like) planar shape around the nozzle 121. The driving method for driving the driving element 13C may be the same as the driving method for driving the driving element 13.

The driving unit 20 can selectively (for example, alternately) apply to the driving element 13C, a discharging waveform for vibrating the membrane 12C to form a liquid droplet 310 and a stirring waveform for vibrating the membrane 12C to an extent until which a liquid droplet 310 is not formed.

For example, the discharging waveform and the stirring waveform may both be rectangular waves, and the driving voltage for the stirring waveform may be set lower than the driving voltage for the discharging waveform. This makes it possible for a liquid droplet 310 not to be formed by application of the stirring waveform. That is, it is possible to control the vibration state (degree of vibration) of the membrane 12C depending on whether the driving voltage is high or low.

In the liquid droplet discharging unit 10C, the driving element 13C is formed on the lower surface of the membrane 12C. Therefore, when the membrane 12 is vibrated by means of the driving element 13C, a flow can be generated in a direction from the lower portion to the upper portion in the liquid chamber 11C.

Here, the fluorescent-stained cells 350 move upward from lower positions, to generate a convection current in the liquid chamber 11C to stir the cell suspension 300 containing the fluorescent-stained cells 350. The flow from the lower portion to the upper portion in the liquid chamber 11C disperses the settled, aggregated fluorescent-stained cells 350 uniformly in the liquid chamber 11C.

That is, by applying the discharging waveform to the driving element 13C and controlling the vibration state of the membrane 12C, the driving unit 20 can cause the cell suspension 300 retained in the liquid chamber 11C to be discharged through the nozzle 121 in the form of a liquid droplet 310. Further, by applying the stirring waveform to the driving element 13C and controlling the vibration state of the membrane 12C, the driving unit 20 can stir the cell suspension 300 retained in the liquid chamber 11C. During stirring, no liquid droplet 310 is discharged through the nozzle 121.

In this way, stirring the cell suspension 300 while no liquid droplet 310 is being formed can prevent settlement and aggregation of the fluorescent-stained cells 350 over the membrane 12C and can disperse the fluorescent-stained cells 350 in the cell suspension 300 without unevenness. This can suppress clogging of the nozzle 121 and variation in the number of fluorescent-stained cells 350 in the liquid droplets 310 to be discharged. This makes it possible to stably discharge the cell suspension 300 containing the fluorescent-stained cells 350 in the form of liquid droplets 310 continuously for a long time.

In the liquid droplet forming device 401C, bubbles may mix in the cell suspension 300 in the liquid chamber 11C. Also in this case, with the atmospherically exposed portion 115 provided at the top of the liquid chamber 11C, the liquid droplet forming device 401C can be evacuated of the bubbles mixed in the cell suspension 300 to the outside air through the atmospherically exposed portion 115. This enables continuous, stable formation of liquid droplets 310 without a need for disposing of a large amount of the liquid for bubble evacuation.

That is, the discharging state is affected when mixed bubbles are present at a position near the nozzle 121 or when many mixed bubbles are present over the membrane 12C. Therefore, in order to perform stable formation of liquid droplets for a long time, there is a need for eliminating the mixed bubbles. Typically, mixed bubbles present over the membrane 12C move upward autonomously or by vibration of the membrane 12C. Because the liquid chamber 11C is provided with the atmospherically exposed portion 115, the mixed bubbles can be evacuated through the atmospherically exposed portion 115. This makes it possible to prevent occurrence of empty discharging even when bubbles mix in the liquid chamber 11C, enabling continuous, stable formation of liquid droplets 310.

At a timing at which a liquid droplet is not being formed, the membrane 12C may be vibrated to an extent until which a liquid droplet is not formed, in order to positively move the bubbles upward in the liquid chamber 11C.

—Electric or Magnetic Detection Method—

Figure 23:
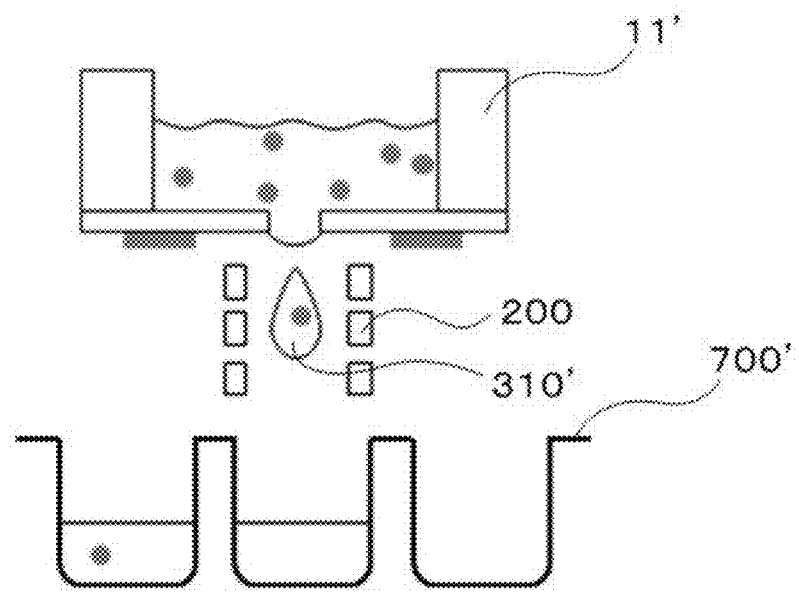
FIG. 23 is an exemplary diagram illustrating another example of a liquid droplet forming device.

In the case of the electric or magnetic detection method, as illustrated in FIG. 23, a coil 200 configured to count the number of cells is installed as a sensor immediately below a discharging head configured to discharge the cell suspension onto a plate 700' from a liquid chamber 11' in the form of a liquid droplet 310'. Cells are coated with magnetic beads that are modified with a specific protein and can adhere to the cells. Therefore, when the cells to which magnetic beads adhere pass through the coil, an induced current is generated to enable detection of presence or absence of the cells in the flying liquid droplet. Generally, cells have proteins specific to the cells on the surfaces of the cells. Modification of magnetic beads with antibodies that can adhere to the proteins enables adhesion of the magnetic beads to the cells. As such magnetic beads, a ready-made product can be used. For example, DYNABEADS (registered trademark) available from Veritas Corporation can be used.

[Operation for Observing Cells Before Discharging]

Figure 24:
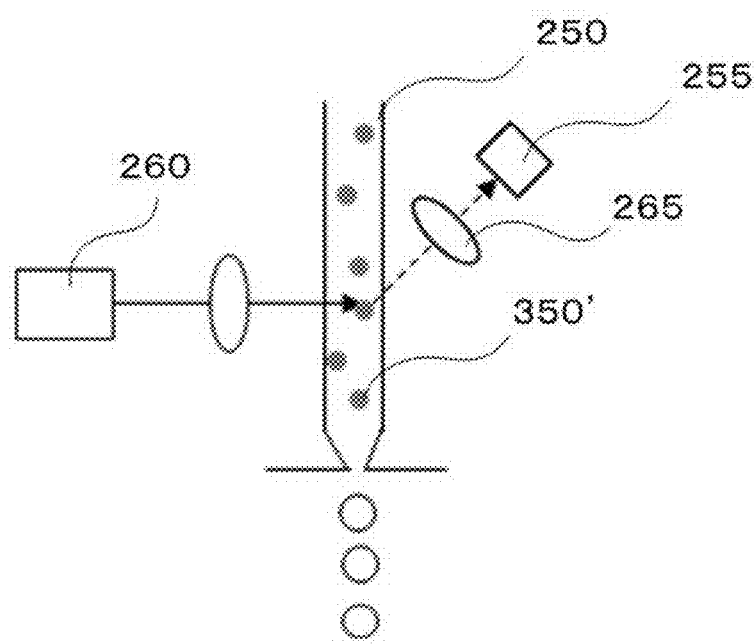
FIG. 24 is an exemplary diagram illustrating an example of a method for counting cells that have passed through a micro-flow path.
Figure 25:
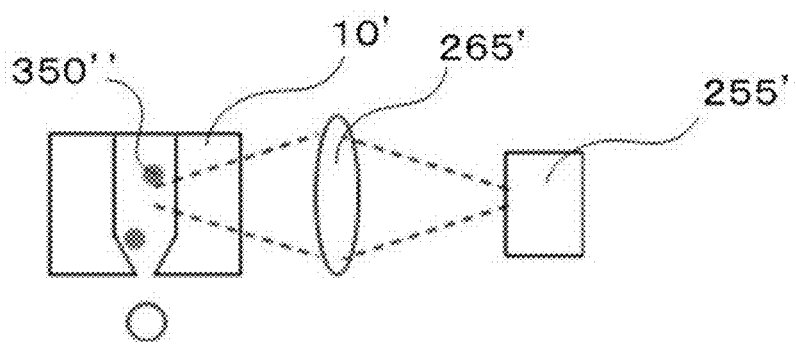
FIG. 25 is an exemplary diagram illustrating an example of a method for capturing an image of a portion near a nozzle portion of a discharging head.

The operation for observing cells before discharging may be performed by, for example, a method for counting cells 350' that have passed through a micro-flow path 250 illustrated in FIG. 24 or a method for capturing an image of a portion near a nozzle portion of a discharging head illustrated in FIG. 25. The method of FIG. 24 is a method used in a cell sorter device, and, for example, CELL SORTER SH800Z available from Sony Corporation can be used. In FIG. 24, a light source 260 emits laser light into the micro-flow path 250, and a detector 255 detects scattered light or fluorescence through a condenser lens 265. This enables discrimination of presence or absence of cells or the kind of the cells, while a liquid droplet is being formed. Based on the number of cells that have passed through the micro-flow path 250, this method enables estimation of the number of cells that have landed in a predetermined well.

As the discharging head 10' illustrated in FIG. 25, a single cell printer available from Cytena GmbH can be used. In FIG. 25, it is possible to estimate the number of cells that have landed in a predetermined well, by capturing an image of the portion near the nozzle portion with an image capturing unit 255' through a lens 265' before discharging and estimating based on the captured image that cells 350" present near the nozzle portion have been discharged, or by estimating the number of cells that are considered to have been discharged based on a difference between images captured before and after discharging. The method of FIG. 25 is more preferable because the method enables on-demand liquid droplet formation, whereas the method of FIG. 24 for counting cells that have passed through the micro-flow path generates liquid droplets continuously.

[Operation for Counting Cells after Landing]

The operation for counting cells after landing may be performed by a method for detecting fluorescent-stained cells by observing the wells in the plate with, for example, a fluorescence microscope. This method is described in, for example, Sangjun et al., PLoS One, Volume 6(3), e17455.

Methods for observing cells before discharging a liquid droplet or after landing have the problems described below. Depending on the kind of the plate to be produced, it is the most preferable to observe cells in a liquid droplet that is being discharged. In the method for observing cells before discharging, the number of cells that are considered to have landed is counted based on the number of cells that have passed through a flow path and image observation before discharging (and after discharging). Therefore, it is not confirmed whether the cells have actually been discharged, and an unexpected error may occur. For example, there may be a case where because the nozzle portion is stained, a liquid droplet is not discharged appropriately but adheres to the nozzle plate, thus failing to make the cells in the liquid droplet land. Moreover, there may occur a problem that the cells stay behind in a narrow region of the nozzle portion, or a discharging operation causes the cells to move beyond assumption and go outside the range of observation.

The method for detecting cells on the plate after landing also have problems. First, there is a need for preparing a plate that can be observed with a microscope. As a plate that can be observed, it is common to use a plate having a transparent, flat bottom surface, particularly a plate having a bottom surface formed of glass. However, there is a problem that such a special plate is incompatible with use of ordinary wells. Further, when the number of cells is large, such as some tens of cells, there is a problem that correct counting is impossible because the cells may overlap with each other. Accordingly, it is preferable to perform the operation for observing cells before discharging and the operation for counting cells after landing, in addition to counting the number of cells contained in a liquid droplet with a sensor and a cell number counting unit after the liquid droplet is discharged and before the liquid droplet lands in a well.

As the light receiving element, a light receiving element including one or a small number of light receiving portion(s), such as a photodiode, an Avalanche photodiode, and a photomultiplier tube may be used. In addition, a two-dimensional sensor including light receiving elements in a two-dimensional array formation, such as a CCD (Charge Coupled Device), a CMOS (Complementary Metal Oxide Semiconductor), and a gate CCD may be used.

Figure 26:
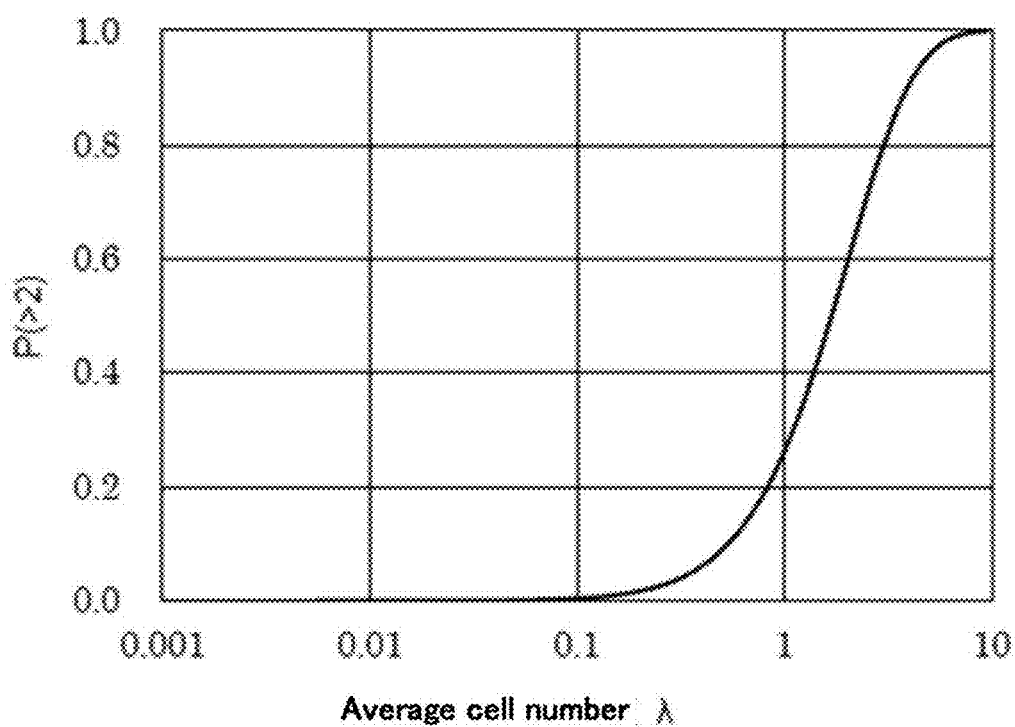
FIG. 26 is a graph plotting a relationship between a probability P (>2) and an average cell number.

When using a light receiving element including one or a small number of light receiving portion(s), it is conceivable to determine the number of cells contained, based on the fluorescence intensity, using a calibration curve prepared beforehand. Here, binary detection of whether cells are present or absent in a flying liquid droplet is common. When the cell suspension is discharged in a state that the cell concentration is so sufficiently low that almost only 1 or 0 cell(s) will be contained in a liquid droplet, sufficiently accurate counting is available by the binary detection. On the premise that cells are randomly distributed in the cell suspension, the cell number in a flying liquid droplet is considered to conform to a Poisson distribution, and the probability P (>2) at which two or more cells are contained in a liquid droplet is represented by a formula (1) below. FIG. 26 is a graph plotting a relationship between the probability P (>2) and an average cell number. Here, A is a value representing an average cell number in a liquid droplet and obtained by multiplying the cell concentration in the cell suspension by the volume of a liquid droplet discharged.

$$P(>2)=1-(1+\lambda)\times e^{-\lambda} \quad \text{formula (1)}$$

When performing cell number counting by binary detection, in order to ensure accuracy, it is preferable that the probability P (>2) be a sufficiently low value, and that $\lambda$ satisfy: $\lambda<0.15$, at which the probability P (>2) is 1% or lower. The light source is not particularly limited and may be appropriately selected depending on the intended purpose, so long as the light source can excite fluorescence from cells. It is possible to use, for example, an ordinary lamp such as a mercury lamp and a halogen lamp to which a filter is applied for emission of a specific wavelength, a LED (Light Emitting Diode), and a laser. However, particularly when forming a minute liquid droplet of 1 nL or less, there is a need for irradiating a small region with a high light intensity. Therefore, use of a laser is preferable. As a laser light source, various commonly known lasers such as a solid-state laser, a gas laser, and a semiconductor laser can be used. The excitation light source may be a light source that is configured to continuously irradiate a region through which a liquid droplet passes or may be a light source that is configured for pulsed irradiation in synchronization with discharging of a liquid droplet at a timing delayed by a predetermined period of time from the operation for discharging the liquid droplet.

<<<Step of Calculating Degrees of Certainty of Estimated Numbers of Nucleic Acids in Cell Suspension Preparing Step, Liquid Droplet Landing Step, and Cell Number Counting Step>>>

The step of calculating degrees of certainty of estimated numbers of nucleic acids in the cell suspension preparing step, the liquid droplet landing step, and the cell number counting step is a step of calculating the degree of certainty in each of the cell suspension preparing step, the liquid droplet landing step, and the cell number counting step.

The degree of certainty of an estimated number of nucleic acids can be calculated in the same manner as calculating the degree of certainty in the cell suspension preparing step.

The timing at which the degrees of certainty are calculated may be collectively in the next step to the cell number counting step, or may be at the end of each of the cell suspension preparing step, the liquid droplet landing step, and the cell number counting step in order for the degrees of certainty to be summed in the next step to the cell number counting step. In other words, the degrees of certainty in these steps need only to be calculated at arbitrary timings by the time when summing is performed.

<<<Outputting Step>>>

The outputting step is a step of outputting a counted value of the number of cells contained in the cell suspension that has landed in a well, counted by a particle number counting unit based on a detection result measured by a sensor.

The counted value means a number of cells contained in the well, calculated by the particle number counting unit based on the detection result measured by the sensor.

Outputting means sending a value counted by a device such as a motor, communication equipment, and a calculator upon reception of an input to an external server serving as a count result memory unit in the form of electronic information, or printing the counted value as a printed matter.

In the outputting step, an observed value or an estimated value obtained by observing or estimating the number of cells or the number of nucleic acids in each well of a plate during production of the plate is output to an external memory unit.

Outputting may be performed at the same time as the cell number counting step, or may be performed after the cell number counting step.

<<<Recording Step>>>

The recording step is a step of recording the observed value or the estimated value output in the outputting step.

The recording step can be suitably performed by a recording unit. Recording may be performed at the same time as the outputting step, or may be performed after the outputting step.

Recording means not only supplying information to a recording medium but also storing information in a memory unit.

<<<Nucleic Acid Extracting Step>>>

The nucleic acid extracting step is a step of extracting nucleic acids from cells in the well.

Extracting means destroying, for example, cellular membranes and cell walls to pick out nucleic acids.

As the method for extracting nucleic acids from cells, there is known a method of thermally treating cells at from 90 degrees C. through 100 degrees C. By a thermal treatment at 90 degrees C. or lower, there is a possibility that DNA may not be extracted. By a thermal treatment at 100 degrees C. or higher, there is a possibility that DNA may be decomposed. Here, it is preferable to perform thermal treatment with addition of a surfactant.

The surfactant is not particularly limited and may be appropriately selected depending on the intended purpose. Examples of the surfactant include ionic surfactants and nonionic surfactants. One of these surfactants may be used alone or two or more of these surfactants may be used in combination. Among these surfactants, nonionic surfactants are preferable because proteins are neither modified nor deactivated by nonionic surfactants, although depending on the addition amount of the nonionic surfactants.

Examples of the ionic surfactants include fatty acid sodium, fatty acid potassium, alpha-sulfo fatty acid ester sodium, sodium straight-chain alkyl benzene sulfonate, alkyl sulfuric acid ester sodium, alkyl ether sulfuric acid ester sodium, and sodium alpha-olefin sulfonate. One of these ionic surfactants may be used alone or two or more of these ionic surfactants may be used in combination. Among these ionic surfactants, fatty acid sodium is preferable and sodium dodecyl sulfate (SDS) is more preferable.

Examples of the nonionic surfactants include alkyl glycoside, alkyl polyoxyethylene ether (e.g., BRIJ series), octyl phenol ethoxylate (e.g., TRITON X series, IGEPAL CA series, NONIDET P series, and NIKKOL OP series), polysorbates (e.g., TWEEN series such as TWEEN 20), sorbitan fatty acid esters, polyoxyethylene fatty acid esters, alkyl maltoside, sucrose fatty acid esters, glycoside fatty acid esters, glycerin fatty acid esters, propylene glycol fatty acid esters, and fatty acid monoglyceride. One of these nonionic surfactants may be used alone or two or more of these nonionic surfactants may be used in combination. Among these nonionic surfactants, polysorbates are preferable.

The content of the surfactant is preferably 0.01% by mass or greater but 5.00% by mass or less relative to the total amount of the cell suspension in the well. When the content of the surfactant is 0.01% by mass or greater, the surfactant can be effective for DNA extraction. When the content of the surfactant is 5.00% by mass or less, inhibition against amplification can be prevented during PCR. As a numerical range in which both of these effects can be obtained, the range of 0.01% by mass or greater but 5.00% by mass or less is preferable.

The method described above may not be able to sufficiently extract DNA from a cell that has a cell wall. Examples of methods for such a case include an osmotic shock procedure, a freeze-thaw method, an enzymic digestive method, use of a DNA extraction kit, an ultrasonic treatment method, a French press method, and a homogenizer method. Among these methods, an enzymic digestive method is preferable because the method can save loss of extracted DNA.

<<<Other Steps>>>

The other steps are not particularly limited and may be appropriately selected depending on the intended purpose. Examples of the other steps include an enzyme deactivating step.

—Enzyme Deactivating Step—

The enzyme deactivating step is a step of deactivating an enzyme. Examples of the enzyme include DNase, RNase, and an enzyme used in the nucleic acid extracting step in order to extract a nucleic acid.

The method for deactivating an enzyme is not particularly limited and may be appropriately selected depending on the intended purpose. A known method can be suitably used.

The device of the present disclosure is widely used in, for example, biotechnology-related industries, life science industries, and health care industries, and can be used suitably for, for example, equipment calibration or generation of calibration curves, and management of the accuracy of a testing device.

In the case of working the device for infectious diseases, the device is applicable to methods stipulated as official analytical methods or officially announced methods.

EXAMPLES

The present disclosure will be described below by way of Examples. The present disclosure should not be construed as being limited to these Examples.

Example 1

<Preparation of Nucleic Acid Sample>
—Production of Dilution Series of High-Concentration Nucleic Acid Samples—

Dilution series of high-concentration nucleic acid samples were prepared, using DNA600-G (available from National Institute of Advanced Industrial Science and Technology, NMIJ CRM 6205-a) as a dense nucleic acid sample, and ULTRAPURE DNASE/RNASE-FREE-DISTILLED WATER (available from Thermo Fisher Scientific Inc., 10977-015, hereinafter referred to as "NFW") as diluent solvent.

The concentrations of the serial dilution samples were determined based on weight measurement of the dense solution and the diluent solvent with an electronic balance (available from A&D Company, Limited, BM-22).

—Production of Yeast Suspension for Series of Low-Concentration Nucleic Acid Samples—
—Gene Recombinant Yeast—

For producing a recombinant, a budding yeast YIL015W BY4741 (available from ATCC, ATCC4001408) was used as a carrier cell for one copy of a specific nucleic acid sequence.

In the form of a plasmid produced by arranging the specific nucleic acid sequence, which was the DNA600-G sequence mentioned above, in tandem with URA3, which was a selectable marker, one copy of the specific nucleic acid sequence was introduced into yeast genome DNA by homologous recombination, targeting a BAR1 region of the carrier cell, to produce a gene recombinant yeast.

—Culturing and Cell-Cycle Control—

In an Erlenmeyer flask, a 90-mL fraction of the gene recombinant yeast cultured in 50 g/L of a YPD medium (available from Takara Bio Inc., CLN-630409) was mixed with 900 microliters of α1-MATING FACTOR ACETATE SALT (available from Sigma-Aldrich Co., LLC, T6901-5 MG, hereinafter referred to as "a factor") prepared to 500 micrograms/mL with a Dulbecco's phosphate buffered saline (available from Thermo Fisher Scientific Inc., 14190-144, hereinafter referred to as "DPBS").

Next, the resultant was incubated with a bioshaker (available from Taitec Corporation, BR-23FH) at a shaking speed of 250 rpm at a temperature of 28 degrees C. for 2 hours, to synchronize the yeast at a G0/G1 phase, to obtain a yeast suspension.

—Fixing—

Forty-five milliliters of the synchronization-confirmed yeast suspension was transferred to a centrifuge tube (available from As One Corporation, VIO-50R) and centrifuged with a centrifugal separator (available from Hitachi, Ltd., F16RN,) at a rotation speed of 3,000 rpm for 5 minutes, with subsequent supernatant removal, to obtain yeast pellets. Four milliliters of formalin (available from Wako Pure Chemical Industries, Ltd., 062-01661) was added to the obtained yeast pellets, and the resultant was left to stand still for 5 minutes, then centrifuged with subsequent supernatant removal, and suspended with addition of 10 mL of ethanol, to obtain a fixed yeast suspension.

—Nuclear Staining—

Two hundred microliters of the fixed yeast suspension was fractionated, washed with DPBS once, and resuspended in 480 microliters of DPBS.

Next, to the resultant, 20 microliters of 20 mg/mL RNase A (available from Nippon Gene Co., Ltd., 318-06391) was added, followed by incubation with a bioshaker at 37 degrees C. for 2 hours.

Next, to the resultant, 25 microliters of 20 mg/mL proteinase K (available from Takara Bio Inc., TKR-9034) was added, followed by incubation with PETIT COOL (available from Waken B Tech Co., Ltd., PETIT COOL MINI T-C) at 50 degrees C. for 2 hours.

Finally, to the resultant, 6 microliters of 5 mM SYTOX GREEN NUCLEIC ACID STAIN (available from Thermo Fisher Scientific Inc., S7020) was added, followed by staining in a light-shielded environment for 30 minutes.

—Dispersing—

The stained yeast suspension was subjected to dispersion treatment using an ultrasonic homogenizer (available from Yamato Scientific Co., Ltd., LUH150,) at a power output of 30% for 10 seconds, to obtain a yeast suspension ink.

<Filling of Nucleic Acid Samples>

—Filling of Series of High-Concentration Nucleic Acid Samples—

The series of high-concentration nucleic acid samples were filled in an amount of 2.5 microliters per well of a filling container (96-well flat bottom plate (available from Watson Co., Ltd., 4846-96-FS)) with a micropipetter (available from Eppendorf AG, 3120000011).

—Filling of Series of Low-Concentration Nucleic Acid Samples—

—Dispensing of Yeast Suspension with Number Counting—

After a filling container (96-well flat bottom plate (available from Watson Co., Ltd., 4846-96-FS)) was filled with a dissolving liquid for dissolving cell walls in an amount of 4 microliters per well beforehand, the series of low-concentration nucleic acid samples were dispensed one cell per well, using a cell sorter (available from Sony Corporation, SH800Z).

Next, with a Tris-EDTA (TE) buffer (available from Thermo Fisher Scientific Inc., AM9861) serving as a cell wall dissolving liquid and ColE1 DNA (available from Nippon Gene Co., Ltd., 312-00434), ColE1/TE was prepared at 5 ng/microliter. With ColE1/TE, a Zymolyase solution of Zymolyase® 100T (available from Nacalai Tesque Inc., 07665-55) was prepared at 1 mg/mL.

Next, during dispensing by a cell sorter, the cell cycle was analyzed at an excitation wavelength of 488 nm, to select only a region in which G0/G1 phase cells were present and dispense a prescribed number of yeast cells by a single cell mode.

—Extraction of Nucleic Acids from Dispensed Yeast Cells—

For extraction of nucleic acids from the yeast cells, the filling container was incubated at 37 degrees C. for 30 minutes, to dissolve the cell walls (extraction of nucleic acids), and then thermally treated at 95 degrees C. for 2 minutes.

<Value Association for Filled Samples>

—Calculation of Uncertainty of Series of High-Concentration Nucleic Acid Samples—

The series of high-concentration nucleic acid samples filled had certain uncertainties for the respective specific copy number levels, due to the following factors of uncertainty.

Factor (1): Uncertainty regarding the concentration of the undiluted DNA600-G solution Uncertainty based on determination of the total mass fraction of nucleic acids by nucleic acid base measurement by an isotopic dilution mass spectrometry (IDMS) and a phosphorus analysis by inductively coupled plasma mass spectrometry (ICP-MS) was associated with the present nucleic acid sample.

Factor (2): Uncertainty of the densities of the diluent solvent and the dense nucleic acid sample solution Factor (3): Uncertainty due to the electronic balance during weight measurement Factor (4): Uncertainty based on a Poisson distribution Factor (5): Uncertainty due to the micropipetter (available from Eppendorf AG) during filling of the nucleic acid samples The uncertainty for each of these factors is presented in Table 2.

A common method for synthesizing uncertainties was employed for synthesizing the uncertainties, and an average specific copy number of the sample finally filled and uncertainty were calculated for each specific copy number level. The results are presented in Table 3.

TABLE 2

| | | Average value | Uncertainty = 1 σ | Unit | Source |
|---|---|---|---|---|---|
| Factor (1) | Copy number concentration of DNA600G | 2.25E+09 | 1.87E+08 | molecules/ microliter | Standard substance certificate from AIST |
| Factor (2) | DNA600G density | 0.997 | 1.00E−05 | mg/ microliter | Standard substance certificate for 25 degrees C. from AIST |
| Factor (2) | Ultrapure water density | 0.99705 | 1.00E−05 | mg/ microliter | 25 degrees C. |
| Factor (3) | Balance | x | 2.50E−03 | mg | AND homepage |
| Factor (4) | Poisson distribution | x | $\sqrt{x}$ | molecules | General formula of Poisson distribution |
| Factor (5) | Micropipetter | 2.5 | 1.00E−02 | microliter | Calibration certificate of micropipetter | n Table 2, the sign "x" in Factor (3) indicates an arbitrary measured value (weight), and the sign "x" in Factor (4) indicates an average specific copy number in which the sample was fractionated (average number of copies filled).

In Table 2, the abbreviation "MST" in Factor (1) and Factor (2) stands for National Institute of Advanced Industrial Science and Technology.

Factor i: Uncertainty regarding a percentage at which the yeast cell number in each discharged liquid droplet matched The uncertainty regarding the factor i was calculated based on the percentage at which the numbers of yeast cells in landed liquid droplets discharged into another container under the same conditions as in the filling method matched the intended numbers of yeast cells. The experiment conditions and results are as described below.

TABLE 3

| | | Sample concentration | Weight Measured | Specific copy number | | |
|---|---|---|---|---|---|---|
| | Kind of liquid | Average value copy/microliter | value mg | Average copy | Uncertainty copy | CV value % |
| 2G | NFW | 0 | 18.60 | | | |
| | Undiluted DNA600G solution | 2.25E+09 | 10.00 | | | |
| | 2G | | 28.60 | 1.96E+09 | 1.63E+08 | 8.3 |
| 200M | NFW | 0 | 91.00 | | | |
| | 2G | 7.85E+08 | 10.00 | | | |
| | 200M | | 101.00 | 1.94E+08 | 1.62E+07 | 8.3 |
| 20M | NFW | 0 | 91.30 | | | |
| | 200M | 7.78E+07 | 10.00 | | | |
| | 20M | | 101.30 | 1.92E+07 | 1.60E+06 | 8.3 |
| 2M | NFW | 0 | 90.80 | | | |
| | 20M | 7.68E+06 | 9.70 | | | |
| | 2M | | 100.50 | 1.85E+06 | 1.54E+05 | 8.3 |
| 200K | NFW | 0 | 91.00 | | | |
| | 2M | 7.41E+05 | 9.70 | | | |
| | 200K | | 100.70 | 1.78E+05 | 1.49E+04 | 8.3 |
| 20K | NFW | 0 | 136.50 | | | |
| | 200K | 7.14E+04 | 15.00 | | | |
| | 20K | | 151.50 | 1.77E+04 | 1.48E+03 | 8.4 |
| 4K | NFW | 0 | 75.90 | | | |
| | 20K | 7.07E+03 | 25.50 | | | |
| | 4K | | 101.40 | 4.44E+03 | 3.76E+02 | 8.5 |
| 1K | NFW | 0 | 75.90 | | | |
| | 4K | 1.78E+03 | 25.40 | | | |
| | 1K | | 101.30 | 1.11E+03 | 9.87E+01 | 8.9 |
| 250 | NFW | 0 | 75.70 | | | |
| | 1K | 4.46E+02 | 25.00 | | | |
| | 250 | | 100.70 | 2.77E+02 | 2.86E+01 | 10.3 |
| 70 | NFW | 0 | 75.70 | | | |
| | 250 | 1.11E+02 | 25.80 | | | |
| | 70 | | 101.50 | 7.03E+01 | 1.03E+01 | 14.7 |

The abbreviations in Table 3 stand for the followings.
2G: diluted solution of the undiluted DNA600G solution
200M: diluted solution of 2G
20M: diluted solution of 200M
2M: diluted solution of 20M
200 k: diluted solution of 2M
20 k: diluted solution of 200 k
4 k: diluted solution of 20 k
1 k: diluted solution of 4 k
250: diluted solution of 1 k
70: diluted solution of 250
NFW: ULTRAPURE DNASE/RNASE-FREE-DISTILLED WATER (available from Thermo Fisher Scientific Inc., 10977-015)

Based on the results in Table 3, it was possible to associate the average copy number of nucleic acids and the uncertainty of the average copy number with the nucleic acid samples filled.

<Calculation of Uncertainty of Series of Low-Concentration Nucleic Acid Samples>

The series of low-concentration nucleic acid samples filled had certain uncertainties for the respective specific copy number levels, due to the following factor of uncertainty.

—Experiment Conditions and Results—

Figure 27A:
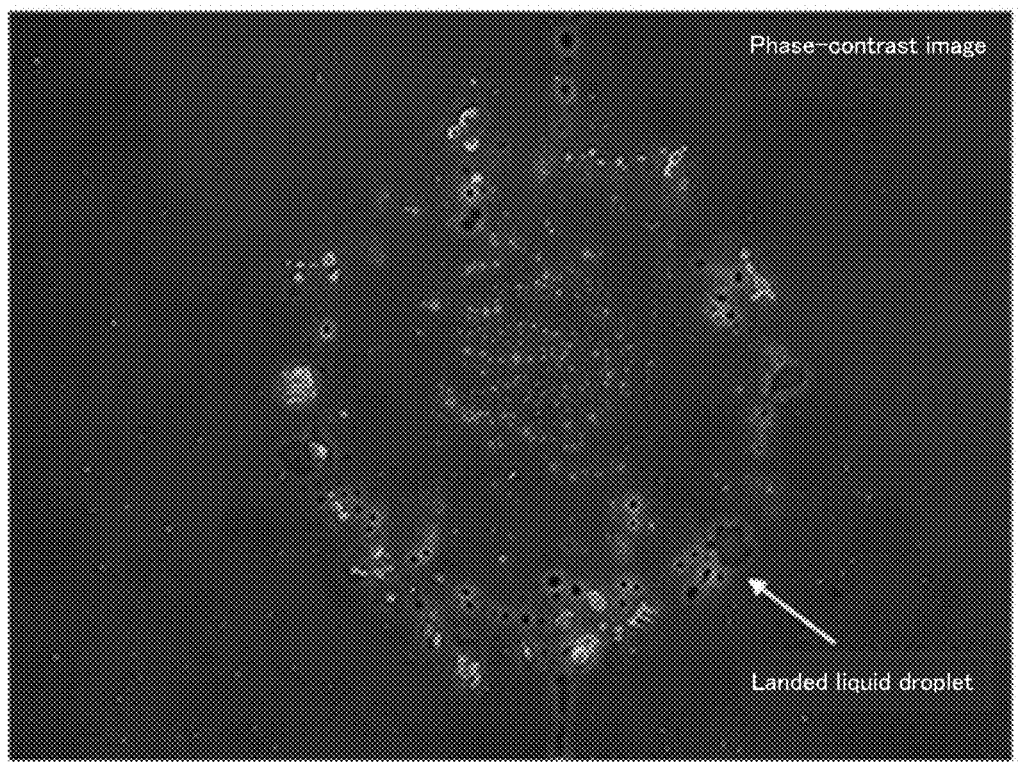
FIG. 27A is a phase-contrast image of a landed liquid droplet of a yeast cell captured with a fluorescence microscope.
Figure 27B:
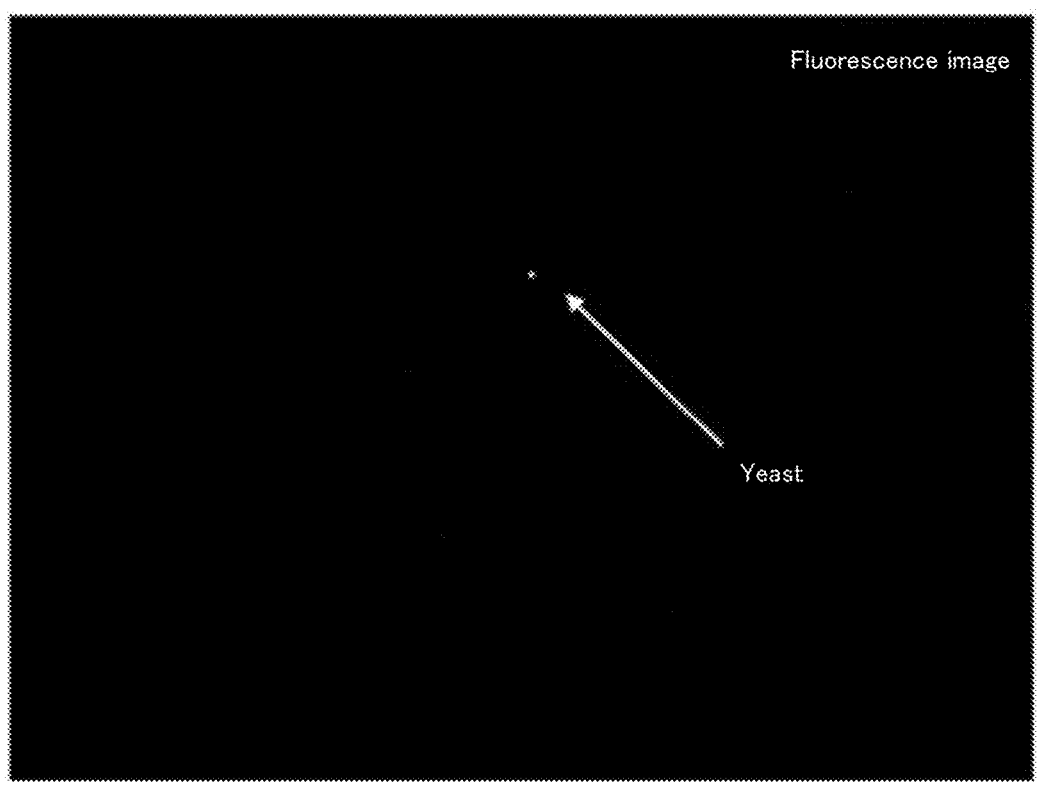
FIG. 27B is a fluorescence image of a landed liquid droplet of a yeast cell captured with a fluorescence microscope.

As a filling container, a 96-well flat bottom plate (available from Watson Co., Ltd., 4846-96-FS) was used. With a cell sorter, one particle (one cell) was dispensed per well under the same conditions as in "Dispensing of yeast suspension with number counting" described above. Subsequently, fluorescence microscopic observation was performed with a fluorescence microscope (available from Carl Zeiss Microscopy GmbH, AXIO OBSERVER D1) with excitation light of 488 nm. The results are presented in FIG. 27A and FIG. 27B. Whether the number of yeast cells present in each liquid droplet and the intended number of yeast cells (1 particle; specific copy number of 1) matched or not was judged, to calculate the matching percentage. The results are presented in Table 4.

TABLE 4

| No. | Intended cell number | Actual cell number | Match or not | No. | Intended cell number | Actual cell number | Match or not |
|---|---|---|---|---|---|---|---|
| 10-1 | 1 | 1 | Match | 12-1 | 1 | 1 | Match |
| 10-2 | 1 | 1 | Match | 12-2 | 1 | 1 | Match |

TABLE 4-continued

| No. | Intended cell number | Actual cell number | Match or not | No. | Intended cell number | Actual cell number | Match or not |
|---|---|---|---|---|---|---|---|
| 10-3 | 1 | 1 | Match | 12-3 | 1 | 1 | Match |
| 10-4 | 1 | 1 | Match | 12-4 | 1 | 1 | Match |
| 10-5 | 1 | 1 | Match | 12-5 | 1 | 1 | Match |
| 10-6 | 1 | 1 | Match | 12-6 | 1 | 1 | Match |
| 10-7 | 1 | 1 | Match | 12-7 | 1 | 1 | Match |
| 10-8 | 1 | 1 | Match | 12-8 | 1 | 1 | Match |
| 10-9 | 1 | 1 | Match | 12-9 | 1 | 1 | Match |
| 10-10 | 1 | 1 | Match | 12-10 | 1 | 1 | Match |
| 10-11 | 1 | 1 | Match | 12-11 | 1 | 1 | Match |
| 10-12 | 1 | 1 | Match | 12-12 | 1 | 1 | Match |
| 10-13 | 1 | 1 | Match | 12-13 | 1 | 1 | Match |
| 10-14 | 1 | 1 | Match | 12-14 | 1 | 1 | Match |
| 10-15 | 1 | 1 | Match | 12-15 | 1 | 1 | Match |
| 10-16 | 1 | 1 | Match | 12-16 | 1 | 1 | Match |
| 10-17 | 1 | 1 | Match | 12-17 | 1 | 1 | Match |
| 10-18 | 1 | 1 | Match | 12-18 | 1 | 1 | Match |
| 10-19 | 1 | 1 | Match | 12-19 | 1 | 1 | Match |
| 10-20 | 1 | 1 | Match | 12-20 | 1 | 1 | Match |
| 10-21 | 1 | 1 | Match | 12-21 | 1 | 1 | Match |
| 10-22 | 1 | 1 | Match | 12-22 | 1 | 1 | Match |
| 10-23 | 1 | 1 | Match | 12-23 | 1 | 1 | Match |
| 10-24 | 1 | 1 | Match | 12-24 | 1 | 1 | Match |
| 10-25 | 1 | 1 | Match | 12-25 | 1 | 1 | Match |
| 10-26 | 1 | 1 | Match | 12-26 | 1 | 1 | Match |
| 10-27 | 1 | 1 | Match | 12-27 | 1 | 1 | Match |
| 10-28 | 1 | 1 | Match | 12-28 | 1 | 1 | Match |
| 10-29 | 1 | 1 | Match | 12-29 | 1 | 1 | Match |
| 10-30 | 1 | 1 | Match | 12-30 | 1 | 1 | Match |
| 10-31 | 1 | 1 | Match | 12-31 | 1 | 1 | Match |
| 10-32 | 1 | 1 | Match | 12-32 | 1 | 1 | Match |
| 10-33 | 1 | 1 | Match | 12-33 | 1 | 1 | Match |
| 10-34 | 1 | 1 | Match | 12-34 | 1 | 1 | Match |
| 10-35 | 1 | 1 | Match | 12-35 | 1 | 1 | Match |
| 10-36 | 1 | 1 | Match | 12-36 | 1 | 1 | Match |
| 10-37 | 1 | 1 | Match | 12-37 | 1 | 1 | Match |
| 10-38 | 1 | 1 | Match | 12-38 | 1 | 1 | Match |
| 10-39 | 1 | 1 | Match | 12-39 | 1 | 1 | Match |
| 10-40 | 1 | 1 | Match | 12-40 | 1 | 1 | Match |
| 10-41 | 1 | 1 | Match | 12-41 | 1 | 1 | Match |
| 10-42 | 1 | 1 | Match | 12-42 | 1 | 1 | Match |
| 10-43 | 1 | 1 | Match | 12-43 | 1 | 1 | Match |
| 10-44 | 1 | 1 | Match | 12-44 | 1 | 1 | Match |
| 10-45 | 1 | 1 | Match | 12-45 | 1 | 1 | Match |
| 10-46 | 1 | 1 | Match | 12-46 | 1 | 1 | Match |
| 10-47 | 1 | 1 | Match | 12-47 | 1 | 1 | Match |
| 10-48 | 1 | 1 | Match | 12-48 | 1 | 1 | Match |
| 10-49 | 1 | 1 | Match | 12-49 | 1 | 1 | Match |
| 10-50 | 1 | 1 | Match | 12-50 | 1 | 1 | Match |
| 10-51 | 1 | 1 | Match | 12-51 | 1 | 1 | Match |
| 10-52 | 1 | 1 | Match | 12-52 | 1 | 1 | Match |
| 10-53 | 1 | 2 | Not (+1) | 12-53 | 1 | 1 | Match |
| 10-54 | 1 | 1 | Match | 12-54 | 1 | 1 | Match |
| 10-55 | 1 | 1 | Match | 12-55 | 1 | 1 | Match |
| 10-56 | 1 | 1 | Match | 12-56 | 1 | 1 | Match |
| 10-57 | 1 | 1 | Match | 12-57 | 1 | 1 | Match |

From the results of Table 4, it was found that the number of yeast cells present in each liquid droplet and the intended number of yeast cells matched at a percentage of 99.2%.

In the present experiment system, the accuracy of the cell sorter for dispensing one yeast cell (specific copy number of 1) per well was 99.2%. In the case of dispensing a greater number of yeast cells (a greater copy number), it is safe to consider that the accuracy for dispensing a specific copy number of yeast cells would be determined by accumulation of the accuracy for one cell.

In the way described above, an average specific copy number and the uncertainty were calculated for each nucleic acid sample filled. The results are presented in Table 5. The coefficient of variation CV was calculated by dividing the uncertainty by the average specific copy number.

TABLE 5

| Specific copy number | | |
|---|---|---|
| Average Copy | Uncertainty Copy | Coefficient of variation CV % |
| 1.01E+00 | 8.80E−02 | 8.74 |
| 2.02E+00 | 1.25E−01 | 6.18 |
| 4.03E+00 | 1.76E−01 | 4.37 |
| 8.06E+00 | 2.49E−01 | 3.09 |
| 1.61E+01 | 3.52E−01 | 2.18 |
| 3.22E+01 | 4.98E−01 | 1.54 |
| 6.45E+01 | 7.04E−01 | 1.09 |
| 1.29E+02 | 9.96E−01 | 0.77 |

—Association of Uncertainty with Each Filled Portion—

The uncertainty calculated in "Calculation of uncertainty of series of high-concentration nucleic acid samples" and "Calculation of uncertainty of series of low-concentration nucleic acid samples" described above was associated with each well.

In this way, it was possible to calculate the average copy number of nucleic acids of the series of high-concentration nucleic acid samples and the series of low-concentration nucleic acid samples and the uncertainty of the average copy number, and associate the average copy number and the uncertainty with each well.

A case of employing an inkjet method in the following manner for filling the series of low-concentration nucleic acid samples will be described. The same method as described above was employed until fixing of the yeast suspension. Therefore, description about the same portion will be skipped.

—Staining—

Five hundred microliters of the fixed yeast suspension was transferred to a 1.5 mL light-shielding tube (available from Watson, 131-915BR), centrifuged with a centrifugal separator at a rotation speed of 3,000 rpm for 5 minutes with subsequent supernatant removal, suspended sufficiently by pipetting with addition of 400 microliters of DPBS (1 mM EDTA) prepared to 1 mM EDTA (available from Tocris Bioscience, 200-449-4), then centrifuged with a centrifugal separator at a rotation speed of 3,000 rpm for 5 minutes with subsequent supernatant removal, to obtain yeast pellets. One milliliter of an Evans blue aqueous solution (available from Wako Pure Chemical Industries, Ltd., 054-04061) prepared to 1 mg/mL was added to the obtained pellets, and the resultant was stirred with a vortex for 5 minutes, then centrifuged with a centrifugal separator at a rotation speed of 3,000 rpm for 5 minutes with subsequent supernatant removal, and stirred with a vortex with addition of DPBS (1 mM EDTA), to obtain a stained yeast suspension.

—Dispersing—

The stained yeast suspension was subjected to dispersion treatment using an ultrasonic homogenizer (available from Yamato Scientific Co., Ltd., device name: LUH150) at a power output of 30% for 10 seconds, centrifuged with a centrifugal separator at a rotation speed of 3,000 rpm for 5 minutes with subsequent supernatant removal, and then washed with addition of 1 mL of DPBS. Centrifugal separation and supernatant removal were performed twice in total, and the resultant was again suspended in 1 mL of DPBS, to obtain a yeast suspension ink.

—Dispensing and Cell Counting—

A plate with known cell numbers was produced by counting the number of yeast cells in liquid droplets in the manner described below to discharge cells into wells in specific copy numbers of 1, 2, 4, 8, 16, 21, 64, and 128. Specifically, with the use of the liquid droplet forming device illustrated in FIG. 19, the yeast suspension ink was sequentially discharged into each well of a 96 plate (product name: MICROAMP 96-WELL REACTION PLATE, available from Thermo Fisher Scientific Inc.), using a piezoelectricity applying-type discharging head (available in-house) as a liquid droplet discharging unit at 10 Hz.

An image of yeast cells in a liquid droplet discharged was captured using a high-sensitivity camera (available from Tokyo Instruments Inc., SCMOS PCO.EDGE) as a light receiving unit and using a YAG laser (available from Spectra-Physics, Inc., EXPLORER ONE-532-200-KE) as a light source, and the cell number was counted by image processing with image processing software IMAGE J serving as a particle number counting unit for the captured image. In this way, a plate with known cell numbers was produced.

—Extraction of Nucleic Acids—

With a Tris-EDTA (TE) buffer and ColE1 DNA (available from Wako Pure Chemical Industries, Ltd., 312-00434), ColE1/TE was prepared at 5 ng/microliter. With ColE1/TE, a Zymolyase solution of Zymolyase® 100T (available from Nacalai Tesque Inc., 07665-55) was prepared at 1 mg/mL.

Four microliters of the Zymolyase solution was added into each well of the produced plate with known cell numbers, incubated at 37.2 degrees C. for 30 minutes, to dissolve cell walls (extraction of nucleic acids), and then thermally treated at 95 degrees C. for 2 minutes, to produce a reference device.

Next, in order to consider the reliability of a result obtained from a plate with a known cell number, a plate with a known cell number, with a cell dispensed in a specific copy number into wells, was produced, and the uncertainty for the cell number of 1 was calculated. Note that it is possible to calculate uncertainties for various copy numbers, by using the method described below for each specific copy number.

—Calculation of Uncertainty—

In the present Example, the number of cells in a liquid droplet, the copy number of amplifiable reagents in a cell, the number of cells in a well, and contamination were used as the factors for uncertainty.

As the number of cells in a liquid droplet, the number of cells in a liquid droplet, counted based on an analysis of an image of the liquid droplet discharged by a discharging unit, and the number of cells obtained based on microscopic observation of each liquid droplet landed on a glass slide among liquid droplets discharged by a discharging unit so as to be landed on the glass slide were used.

The copy number of nucleic acids in a cell (cell cycle) was calculated using the ratio of cells that were at a G1 phase of the cell cycle (99.5%) and the ratio of cells that were at a G2 phase (0.5%).

As the number of cells in a well, the number of discharged liquid droplets landed in a well was counted. However, in counting 96 samples in total, all of the samples were landed in the wells as liquid droplets. Therefore, as a factor, the number of cells in a well was excluded from calculation of the uncertainty.

To confirm contamination, a filtrate (4 microliters) of the ink was subjected to real-time PCR to see whether any other nucleic acid than the amplifiable reagents in the cell was mixed in the ink liquid. This was tried three times. The result was the limit of detection in all of the three tries. Therefore, as a factor, contamination was also excluded from calculation of the uncertainty.

For the uncertainty, standard deviation was calculated from the measured values of each factor and multiplied by a sensitivity coefficient, to obtain a standard uncertainty unified in the unit of the measured quantity. Based on such standard uncertainties, a synthesized standard uncertainty was calculated according to the sum-of-squares method. The synthesized standard uncertainty covered only the values in a range of about 68% of a normal distribution. Therefore, by doubling the synthesized standard uncertainty, it was possible to obtain an expanded uncertainty, which was an uncertainty that took into account a range of about 95% of the normal distribution. The results are presented in the budget sheet of Table 6 below.

TABLE 6

| Symbol | Factors of uncertainty | Value (±) | Probability distribution | Divisor | Standard uncertainty | Sensitivity coefficient | Standard uncertainty (in unit of measured quantity) |
|---|---|---|---|---|---|---|---|
| u1 | Number of cells in liquid droplet | 0.1037 cells | — | 1 | 0.1037 cells | 1.0290 copies/cell | 0.1067 copies |
| u2 | Number of nucleic acid molecules in cell (cell cycle) | 0.0709 Copies | — | 1 | 0.0709 copies | — | 0.0709 copies |
| u3 | Number of cells in well | — | — | — | — | — | — |
| u4 | Contamination | — | — | — | — | — | — |
| uc | Synthesized standard uncertainty | | Normal distribution | | | | 0.1281 copies |
| u | Expanded uncertainty | | Normal distribution (k = 2) | | | | 0.2562 copies |

In Table 6, "Symbol" means an arbitrary symbol associated with a factor of the uncertainty.

In Table 6, "Value (±)" indicates an experimental standard deviation in average value, obtained by dividing a calculated experimental standard deviation by the square root of the number of data.

In Table 6, "Probability distribution" is a probability distribution of a factor of the uncertainty. The field was left blank for type-A uncertainty evaluation, whereas either normal distribution or rectangular distribution was filled in the field for type-B uncertainty evaluation. In the present Example, only type-A uncertainty evaluation was performed. Therefore, the probability distribution field was left blank.

In Table 6, "Divisor" means a number that normalizes the uncertainty of each factor.

In Table 6, "Standard uncertainty" is a value obtained by dividing "Value (±)" by "Divisor".

In Table 6, "Sensitivity coefficient" means a value used for unification to the unit of the measured quantity.

Next, the average specific copy number and the uncertainty were calculated for the nucleic acid sample filled in the wells. The results are presented in Table 7. The coefficient of variation CV was calculated by dividing the uncertainty by the average specific copy number.

TABLE 7

| Specific copy number | | |
| --- | --- | --- |
| Average Copy | Uncertainty Copy | Coefficient of variation CV % |
| 1.02E+00 | 1.28E−01 | 12.60 |
| 2.03E+00 | 1.81E−01 | 8.91 |
| 4.07E+00 | 2.56E−01 | 6.30 |
| 8.13E+00 | 3.62E−01 | 4.46 |
| 1.63E+01 | 5.12E−01 | 3.15 |
| 2.13E+01 | 5.87E−01 | 2.75 |
| 6.50E+01 | 1.02E+00 | 1.58 |
| 1.30E+02 | 1.45E+00 | 1.11 |

It was found that the accuracy of the inkjet method for dispensing one copy of a nucleic acid sample (one yeast cell) in the specific copy number of 1 into wells was ±0.1281 copies. In the case of filling one or more copies into a well, the accuracy for filling a nucleic acid sample in the specific copy number would be determined by accumulation of this accuracy.

From the results described above, the obtained expanded uncertainty was stored as data of the device as the indicator of the variation in measurement. This would enable a user to use the indicator of the uncertainty as the reference for judging the reliability of a result of measurement in each well in an experiment. Use of the reference for judging the reliability would enable highly accurate evaluation of the performance of an analytical test.

The embodiments of the present disclosure are, for example, as follows

<1> A device including:

at least one well in which an amplifiable reagent is contained in a specific copy number of less than 100; and at least one well in which the amplifiable reagent is contained in a specific copy number of 100 or greater, wherein for at least one well in which the specific copy number of the amplifiable reagent is less than 100, a formula: $CV<1/\sqrt{x}$ is established, where CV represents a coefficient of variation for the specific copy number and x represents average specific copy number of the amplifiable reagent.

<2> The device according to <1>, wherein a coefficient of variation CV of the at least one well in which the specific copy number of the amplifiable reagent is 100 or greater is 20% or lower.

<3> The device according to <1> or <2>, wherein a coefficient of variation CV of the at least one well in which the specific copy number of the amplifiable reagent is less than 100 is 10% or lower.

<4> The device according to any one of <1> to <3>, wherein for the specific copy number of the amplifiable reagent of 100 or greater, a formula: $CV>1/\sqrt{x}$ is established, where CV represents a coefficient of variation for the specific copy number and x represents average specific copy number of the amplifiable reagent.

<5> The device according to any one of <1> to <4>, wherein each of the specific copy numbers of the amplifiable reagent contained in the at least one well includes two or more levels.

<6> The device according to any one of <1> to <5>, further including for a specific copy number of the amplifiable reagent in the at least one well, information on uncertainty of the specific copy number.

<7> The device according to <6>, further including an identifier unit configured to enable identifying at least any one of information on the coefficient of variation CV of the at least one well in which the specific copy number of the amplifiable reagent is less than 100, information on the coefficient of variation CV of the at least one well in which the specific copy number of the amplifiable reagent is 100 or greater, and the information on the uncertainty of the specific copy number.

<8> The device according to any one of <1> to <7>, further including a sealing member configured to seal an opening of the at least one well.

<9> The device according to <8>, wherein the amplifiable reagent is a nucleic acid.

<10> The device according to <9>, wherein the nucleic acid is incorporated into a nucleic acid in a nucleus of a cell.

<11> The device according to <10>, wherein the cell is a yeast cell.

<12> The device according to any one of <1> to <11>, wherein the at least one well contains at least any one of a primer and an amplifying reagent.

<13> The device according to any one of <9> to <12>, wherein the at least one well includes a plurality of wells, and wherein the device further includes a specific copy number of the nucleic acid in each of the plurality of wells and the uncertainty of the specific copy number of the nucleic acid, as information for each of the plurality of wells.

<14> The device according to any one of <8> to <13>, further including a base material provided with the at least one well, wherein the identifier unit is placed between the sealing member and the base material.

<15> A device including;

at least one well; and information on a specific copy number of a nucleic acid in the at least one well and uncertainty of the specific copy number of the nucleic acid, wherein the device is used for evaluation of a PCR device capable of amplifying a nucleic acid.

<16> The device according to <15>,
wherein a result of amplification of a nucleic acid by the device and the information on the specific copy number of the nucleic acid and the uncertainty of the specific copy number of the nucleic acid are used for management of the PCR device.

The device according to any one of <1> to <14> and the device according to <15> or <16> can solve the various problems in the related art and can achieve the object of the present disclosure.

What is claimed is:

1. A kit comprising:
   at least one well containing an amplifiable reagent at a specific copy number of less than 100; and
   at least one well containing the amplifiable reagent at a specific copy number of 100 or greater,
   wherein for the at least one well in which the specific copy number of the amplifiable reagent is less than 100, a formula: $CV<1/\sqrt{x}$ is established, where CV represents a coefficient of variation for the specific copy number and x represents average specific copy number of the amplifiable reagent.

2. The kit according to claim 1,
   wherein a coefficient of variation CV of the at least one well in which the specific copy number of the amplifiable reagent is 100 or greater is 20% or lower.

3. The kit according to claim 1,
   wherein a coefficient of variation CV of the at least one well in which the specific copy number of the amplifiable reagent is less than 100 is 10% or lower.

4. The kit according to claim 1,
   wherein for the specific copy number of the amplifiable reagent of 100 or greater, a formula: $CV<1/\sqrt{x}$ is established, where CV represents a coefficient of variation for the specific copy number and x represents average specific copy number of the amplifiable reagent.

5. The kit according to claim 1,
wherein each of the specific copy numbers of the amplifiable reagent contained in the at least one well includes two or more levels.

6. The kit according to claim 1, further comprising
for a specific copy number of the amplifiable reagent in the at least one well, information on uncertainty of the specific copy number.

7. The kit according to claim 6, further comprising
an identifier unit configured to enable identifying at least any one of information on the coefficient of variation CV of the at least one well in which the specific copy number of the amplifiable reagent is less than 100, information on the coefficient of variation CV of the at least one well in which the specific copy number of the amplifiable reagent is 100 or greater, and the information on the uncertainty of the specific copy number.

8. The kit according to claim 1, further comprising
a sealing member configured to seal an opening of the at least one well.

9. The kit according to claim 8,
wherein the amplifiable reagent is a nucleic acid.

10. The kit according to claim 9,
wherein the nucleic acid is incorporated into a nucleic acid in a nucleus of a cell.

11. The kit according to claim 10,
wherein the cell is a yeast cell.

12. The kit according to claim 1,
wherein the at least one well contains at least any one of a primer and an amplifying reagent.

13. The kit according to claim 9,
wherein the at least one well comprise a plurality of wells, and
wherein the kit further comprises a specific copy number of the nucleic acid in each of the plurality of wells and the uncertainty of the specific copy number of the nucleic acid, as information for each of the plurality of wells.

14. The kit according to claim 8, further comprising
a base material provided with the at least one well,
wherein the identifier unit is placed between the sealing member and the base material.

15. A kit comprising:
at least one well having a nucleic acid contained therein; and
information on a specific copy number of the nucleic acid and uncertainty of the specific copy number of the nucleic acid,
wherein the kit is used for evaluation of a PCR device capable of amplifying a nucleic acid.

16. The kit according to claim 15,
wherein a result of amplification of a nucleic acid by the kit and the information on the specific copy number of the nucleic acid and the uncertainty of the specific copy number of the nucleic acid are used for management of the PCR device.

* * * * *